United States Patent
Beswick et al.

(10) Patent No.: US 7,612,201 B2
(45) Date of Patent: Nov. 3, 2009

(54) PYRAZOLE COMPOUNDS

(75) Inventors: Mandy Christine Beswick, Harlow (GB); Martin James Drysdale, Abington (GB); Brian William Dymock, Abingdon (GB); Edward McDonald, London (GB)

(73) Assignees: Vernalis (Cambridge) Limited (GB); Cancer Research Technology Ltd. (GB); The Institute of Cancer Research (GB)

( * ) Notice: Subject to any disclaimer, the term of this patent is extended or adjusted under 35 U.S.C. 154(b) by 315 days.

(21) Appl. No.: 10/536,899

(22) PCT Filed: Dec. 18, 2003

(86) PCT No.: PCT/GB03/05501

§ 371 (c)(1),
(2), (4) Date: Jan. 6, 2006

(87) PCT Pub. No.: WO2004/056782

PCT Pub. Date: Jul. 8, 2004

(65) Prior Publication Data

US 2006/0148817 A1    Jul. 6, 2006

(30) Foreign Application Priority Data

Dec. 19, 2002    (GB) ................... 0229618.4

(51) Int. Cl.
  C07D 231/38    (2006.01)
  C07D 401/04    (2006.01)
  C07D 403/04    (2006.01)
  C07D 405/12    (2006.01)
  C07D 409/12    (2006.01)
  C07D 417/12    (2006.01)

(52) U.S. Cl. ................... 544/121; 544/60; 544/140; 544/364; 544/367; 544/370; 544/371; 546/210

(58) Field of Classification Search .............. None
See application file for complete search history.

(56) References Cited

U.S. PATENT DOCUMENTS 5,486,534 A * 1/1996 Lee et al. .............. 514/406

FOREIGN PATENT DOCUMENTS

| DE | 10307329 | * | 8/2004 |
| JP | 63 253068 A | | 10/1988 |
| WO | 96 03385 | | 2/1996 |
| WO | WO 97 01551 A | | 1/1997 |
| WO | WO 98 52940 A | | 11/1998 |
| WO | WO 00 31063 A | | 6/2000 |
| WO | WO 01 79187 A | | 10/2001 |
| WO | WO 03 055860 A | | 7/2003 |
| WO | WO 03 062206 A | | 7/2003 |

OTHER PUBLICATIONS

Vippagunta et al. Advanced Drug Delivery Reviews, vol. 48, p. 3-26 (2001).*
Barril et al. Bioorganic & Medicinal Chemistry Letters, vol. 16, pp. 2543-2548 (2006).*
Dymock et al. Expert Opin.Ther.Patents, vol. 14(6), pp. 837-847 (2004). Available online at http://www.expertopin.com/doi/pdf/10.1517/13543776.14.6.837.*

(Continued)

Primary Examiner—Emily Bernhardt
(74) Attorney, Agent, or Firm—Banner & Witcoff, Ltd.

(57) ABSTRACT

Compounds of formula (IA) or (IB) or a salt, N-oxide, hydrate or solvate thereof are inhibitors of HSP90, and are of value in the treatment of diseases responsive to HSP90 inhibition such as cancers. In the formulae, Ar is an aryl, aryl($C_1$-$C_6$ alkyl), aryl($C_1$-$C_6$ alkyl), heteroaryl, heteroarylaryl($C_1$-$C_6$ alkyl), or heteroarylaryl($C_1$-$C_6$ alkyl) group, any of which being optionally substituted in the aryl or heteroaryl part thereof; $R_1$, is hydrogen or optionally substituted $C_1$-$C_6$ alkyl; $R_2$ is hydrogen, optionally substituted cycloalkyl, cycloalkenyl, $C_1$-$C_6$ alkyl, $C_1$-$C_6$ alkenyl, or $C_1$-$C_6$ alkynyl; or a carboxyl, carboxamide or carboxyl ester group; and ring A is a non aromatic carbocyclic or heterocyclic ring wherein (i) a ring carbon is optionally substituted, and/or (ii) a ring nitrogen is optionally substituted by a group of formula -$(Alk^1)_p$ $(Cyc)_n$-$(Alk^3)_m$-$(Z)r$ $(Alk^2)_s$ Q where $Alk^1$, $Alk^2$ and $Alk^3$ are optionally substituted $C_1$-$C_3$ alkyl, Cyc is an optionally substituted carbocyclic or heterocyclic radical; m, n, p, r and s are independently 0 or 1, Z is -0-, —S—, —(C=O)—, —S02-, —C(=O)O—, —OC(=O)—, —NW—, —C(=O)NRA-, —$NR^A$C(=O)—, —$SO_2NR^A$—, or —$NR^ASO_2$— wherein $R^A$ is hydrogen or $C_1$-$C_6$ alkyl, and Q is hydrogen or an optionally substituted carbocyclic or heterocyclic radical.

(IA)

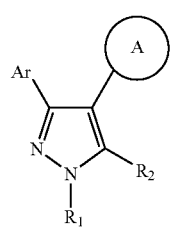

(IB)

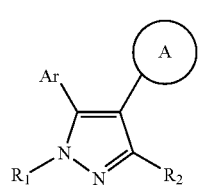

7 Claims, No Drawings

OTHER PUBLICATIONS

Database Chemcats 'Online! American Chemical Society; retrieved from STN, XP002275488, RNs 512817-94-6, dated May 19, 2003; 512812-41-8, dated May 19, 2003; 512817-19-5, dated May 19, 2003; 512817-26-4, dated May 19, 2003; 494867-78-6, dated Apr. 29, 2003.

Database Chemcats 'Online! American Chemical Society; retrieved from STN, XP002275489 RNs 494867-81-1, dated Jul. 9, 2002; 442643-27-8, dated Jul. 9, 2002; 442642-90-2, dated Jul. 9, 2002; 430450-02-5, dated Jan. 17, 2002; 442643-55-2, dated Jan. 17, 2002; 426252-69-9, dated Jul. 9, 2002; 426246-04-7, dated Jul. 9, 2002; 428478-82-4, dated Jul. 9, 2002, 2002; 426242-81-1, dated Jul. 9, 2002; 426241-82-9, dated Jul. 9, 2002; 428480-97-1, dated Jan. 17, 2002; 428479-84-9 dated Jan. 17, 2002.

Patent Abstracts of Japan vol. 013, No. 061 (C-567), Feb. 10, 1989.

Database CA 'Online! Chemical Abstracts Service, Columbus, Ohio, US; Sausins, A, et al: "Methods of synthesis of 4-(pyrazolyl)- and 4-(pyridyl)-5-oxo-1,4,5,7-tetrahydrofuro'3,4- b!pyridines" retrieved from STN, Database accession no. 124:202067 XP002275490, RNs 154926-86-0, 174314-90-0, 174314-91-1,174314-93-3, 174314-96-6, 174314-97-7, 174314-98-8 & Khimiya Geterotsiklicheskikh Soedinenii (1995), (7), 966-72.

Database CA 'Online! Chemical Abstracts Service, Columbus, Ohio, US; Baraldi, P.G. et al: 'Synthesis and cardiodepressant activity of dialkyl 1, 4-dihydro-2, 6-dimethyl-4-(pentatomic-heteroaryl)-3,5-pyridinedicarboxylates. 2 retrieved from STN, Database accession No. 120:289435, XP002275491 abstract; RN 154926-86-0 & Drug Design and Discovery (1993), 10(4), 319-29.

Database CA 'Online! Chemical Abstracts Service, Columbus, Ohio, US; Shanker, M.S.S. et al: "A novel synthesis of pyrazolylchromone derivatives" retrieved from STN, Database accession No. 116:128767 XP002275492 RN 139394-43-7 & Asian Journal of Chemistry (1992), 4(1), 166-70.

Database CA 'Online! Chemical Abstracts Service, Columbus, Ohio, US; Cekavicius, B et al: "Synthesis and hepatoprotective properties of 4-pyrazolyl-1, 4-dihydropyridines" retrieved from STN, Database accession No. 108:68683, XP002275493 abstract; RN 112758-37-9 & Khimiko-Farmatsevticheskii Zhurnal (1987), 21(8), 959-65,.

Database CA 'Online! Chemical Abstracts Service, Columbus, Ohio, US; Hoffmann, Michael G. et al: "O-Glycosylimidates. 19. Reaction of glycosyltrichloroacetimidates with silylated C-nucleophiles" retrieved from STN, Database accession No. 104:51038, XP002275494 RNs 99701-82-3, 99701-81-2, 99701-83-4 & Liebigs Annalen Der Chemie (1985), (12), 2403-19.

Database CA 'Online! Chemical Abstracts Service, Columbus, Ohio, US; Alonso, G. et al: "Synthesis of pyrazole C-nucleosides by 1,3-dipolar cycloaddition" retrieved from STN Database accession No. 87:184819, XP002275495 RN 64559-22-4 & Anales De Quinica (1968-1979) (1976), 72(11-12), 987-90.

Database CA 'Online! Chemical Abstracts Service, Columbus, Ohio, US; Arakawa, Kiichi. et al: "Synthesis of 1-(3-phenylpyrazol-4-yl) beta.-D-ribofuranoside, a C-nucleoside" retrieved from STN, Database accession No. 82:73382, XP002275496 RNs 54680-27-2, 54680-28-3, 54680-29-4, 54680-30-7& Chemistry Letters (1974), (11), 1305-8.

Database CA 'Online! Chemical Abstracts Service, Columbus, Ohio, US; Garcia-Lopez, M. T.. et al: "Synthesis of heterocyclic C-glycosyl compounds by 1,3-dipolar cycloaddition of diazomethane to acetylenic-carbohydrate derivatives" retrieved from STN, Database accession No. 75:88530, XP002275497 RNs 34020-52-5, 34020-53-6 & Journal of Heterocyclic Chemistry (1971), 8(3), 525.

Database CA 'Online! Chemical Abstracts Service, Columbus, Ohio, US; Terent'EV, P.B.. et al: "Addition of diazomethane to.beta.-ethynylpyridines" retrieved from STN, Database accession No. 73:45406, XP002275498, RN 27509-32-6 & Khimiya Geterotsiklicheskikh Soedinenii (1970), (4), 498-502.

Database CA 'Online! Chemical Abstracts Service; Columbus, Ohio, US; Borrachero-Moya, Pastora et al: "Synthesis of 4-(4,6-di-0-benzyl-2,3-dideoxy-.beta.-D-erythro-hex-2-enopyranosyl) pyrazoles from 3,4,6-tri-0-acetyl-D-glucal" retrieved from STN, Database accession No. 129:189545, XP002275499; RNs 211674-08-7, 211674-06-5, 211674-15-6 & Carbohydrate Research (1998), 308(1-2), 181-190.

Database CA 'Online! Chemical Abstracts Service, Columbus, Ohio, US; Baraldi, P.G.. et al: "Synthesis and cardiodepressant activity of dialkyl 1, 4-dihydro-2, 6-dimethyl-4-(pentatomic-heteroaryl)-3, 5-pyridinedicarboxylates, 2" retrieved from STN, Database accession No. 120:289435, XP002275500, RN 154926-87-1 & Drug Design and Discovery (1993), 10(4), 319-29.

Database CA 'Online! Chemical Abstracts Service, Columbus, Ohio, US; Ghosh, Chandra Kanta et al: "Benzopyrans. 31. Reaction of 1,1-diacetyl-2-(6-methyl-4-0x0-4H-1-benzopyran-3-yl)ethylene with phenyldiazomethane" retrieved from STN Database accession No. 119:270955, XP002275501 RN 151466-29-4 & Tetrahedron (1993), 49(19), 4135-40.

Database CA 'Online! Chemical Abstracts Service, Columbus, Ohio, US; Moreno-Manas, Marcial. et al: "Hindered rotation around C(sp3) bonds in the enol forms of. alpha.-(9-fluorenyl)-.beta.-diketones and in 3,5-disubstituted 4-(9-fluorenyl)pyrazoles. A proton NMR study" retrieved from STN, Database accession No. 110:74500, XP002275502 RN 118365-08-5 & Bulletin of the Chemical of Japan (1988), 61(5), 1827-9.

Database CA 'Online! Chemical Abstracts Service, Columbus, Ohio, US; Gonzalez, A... et al: "Metal complexes in organic synthesis. Preparation of. Alpha.-(1-adamantyl)-.beta.-dicarbonyl compounds and 4-(1-adamanty1)-3, 5-disubstituted pyrazoles and-1 soxazoles" retrieved from STN, Database accession No. 106:213817, XP002275503 RN 108221-13-2, & Tetrahedron (1986), 42(15), 4253-7.

Database CA 'Online! Chemical Abstracts Service, Columbus, Ohio, US; Bobowski, George.. et al: "4-Substituted-3-alkyl-3, 4-dihydro-2H-1, 3-benzoxazin-2-ones. IV. Keto-enol tautomerism of. Beta.-keto ester derivatives. Reaction of. Beta.-dicarbonyl compounds with diamines" retrieved from STN Database accession No. 93:168205, XP002275504, RN 74834-76-4 & Journal of Heterocyclic Chemistry (1980), 17(3), 519-28.

Bannier A. et al: "Determination of a New Anti-Inflammatory Agent, 1-Isobutyl-3, 4-Diphenylpyrazole-5-Acetic Acid, by High-Performance Liquid Chromatography" Journal of Physiology, XX, XX, vol. 227, No. 1, Jan. 8,1982, pp. 213-218, XP009008354; ISSN: 0022-3751.

* cited by examiner

PYRAZOLE COMPOUNDS

This application is a U.S. National Stage application of co-pending PCT application PCT/GB2003/005501, filed Dec. 18, 2003, which claims the priority of Great Britain Patent Application No. 0229618.4, filed Dec. 19, 2002. These applications are incorporated herein by reference in their entireties.

This invention relates to substituted pyrazoles having HSP90 inhibitory activity, to the use of such compounds in medicine, in relation to diseases which are responsive to inhibition of HSP90 activity such as cancers, and to pharmaceutical compositions containing such compounds.

BACKGROUND TO THE INVENTION

Molecular chaperones maintain the appropriate folding and conformation of proteins and are crucial in regulating the balance between protein synthesis and degradation. They have been shown to be important in regulating many important cellular functions, such as cell proliferation and apoptosis (Jolly and Morimoto, 2000; Smith et al., 1998; Smith, 2001).

Heat Shock Proteins (HSPs)

Exposure of cells to a number of environmental stresses, including heat shock, alcohols, heavy metals and oxidative stress, results in the cellular accumulation of a number of chaperones, commonly known as heat shock proteins (HSPs). Induction of HSPs protects the cell against the initial stress insult, enhances recovery and leads to maintenance of a stress tolerant state. It has also become clear, however, that certain HSPs may also play a major molecular chaperone role under normal, stress-free conditions by regulating the correct folding, degradation, localization and function of a growing list of important cellular proteins.

A number of multigene families of HSPs exist, with individual gene products varying in cellular expression, function and localization. They are classified according to molecular weight, e.g., HSP70, HSP90, and HSP27.

Several diseases in humans can be acquired as a result of protein misfolding (reviewed in Tytell et al., 2001; Smith et al., 1998). Hence the development of therapies which disrupt the molecular chaperone machinery may prove to be beneficial. In some conditions (e.g., Alzheimer's disease, prion diseases and Huntington's disease), misfolded proteins can cause protein aggregation resuming in neurodegenerative disorders. Also, misfolded proteins may result in loss of wild type protein function, leading to deregulated molecular and physiological functions in the cell.

HSPs have also been implicated in cancer. For example, there is evidence of differential expression of HSPs which may relate to the stage of tumour progression (Martin et al., 2000; Conroy et al., 1996; Kawanishi et al., 1999; Jameel et al., 1992; Hoang et al., 2000; Lebeau et al., 1991). As a result of the involvement of HSP90 in various critical oncogenic pathways and the discovery that certain natural products with anticancer activity are targeting this molecular chaperone, the fascinating new concept has been developed that inhibiting HSP function may be useful in the treatment of cancer. The first molecular chaperone inhibitor is currently undergoing clinical trials.

HSP90

HSP90 constitutes about 1-2% of total cellular protein, and is usually present in the cell as a dimer in association with one of a number of other proteins (see, e.g., Pratt, 1997). It is essential for cell viability and it exhibits dual chaperone functions (Young et al., 2001). It plays a key role in the cellular stress response by interacting with many proteins after their native conformation has been altered by various environmental stresses, such as heat shock, ensuring adequate protein folding and preventing non-specific aggregation (Smith et al., 1998). In addition, recent results suggest that HSP90 may also play a role in buffering against the effects of mutation, presumably by correcting the inappropriate folding of mutant proteins (Rutherford and Lindquist, 1998). However, HSP90 also has an important regulatory role. Under normal physiological conditions, together with its endoplasmic reticulum homologue GRP94, HSP90 plays a housekeeping role in the cell, maintaining the conformational stability and maturation of several key client proteins. These can be subdivided into three groups: (a) steroid hormone receptors, (b) Ser/Thr or tyrosine kinases (e.g., ERBB2, RAF-1, CDK4, and LCK), and (c) a collection of apparently unrelated proteins, e.g., mutant p53 and the catalytic subunit of telomerase hTERT. All of these proteins play key regulatory roles in many physiological and biochemical processes in the cell. New HSP90 client proteins are continuously being identified.

The highly conserved HSP90 family in humans consists of four genes, namely the cytosolic HSP90α and HSP90β isoforms (Hickey et al., 1989), GRP94 in the endoplasmic reticulum (Argon et al., 1999) and HSP75/TRAP1 in the mitochondrial matrix (Felts et al., 2000). It is thought that all the family members have a similar mode of action, but bind to different client proteins depending on their localization within the cell. For example, ERBB2 is known to be a specific client protein of GRP94 (Argon et al., 1999) and type 1 tumour necrosis factor receptor (TNFR1) and RB have both been shown to be clients of TRAP1 (Song et al., 1995; Chen et al., 1996).

HSP90 participates in a series of complex interactions with a range of client and regulatory proteins (Smith, 2001). Although the precise molecular details remain to be elucidated, biochemical and X-ray crystallographic studies (Prodromou et al., 1997; Stebbins et al., 1997) carried out over the last few years have provided increasingly detailed insights into the chaperone function of HSP90.

Following earlier controversy on this issue, it is now clear that HSP90 is an ATP-dependent molecular chaperone (Prodromou et al, 1997), with dimerization of the nucleotide binding domains being essential for ATP hydrolysis, which is in turn essential for chaperone function (Prodromou et al, 2000a). Binding of ATP results in the formation of a toroidal dimer structure in which the N terminal domains are brought into closer contact with each other resulting in a conformational switch known as the 'clamp mechanism' (Prodromou and Pearl, 2000b).

Known HSP90 Inhibitors

The first class of HSP90 inhibitors to be discovered was the benzoquinone ansamycin class, which includes the compounds herbimycin A and geldanamycin. They were shown to reverse the malignant phenotype of fibroblasts transformed by the v-Src oncogene (Uehara et al., 1985), and subsequently to exhibit potent antitumour activity in both in vitro (Schulte et al., 1998) and in vivo animal models (Supko et al., 1995).

Immunoprecipitation and affinity matrix studies have shown that the major mechanism of action of geldanamycin involves binding to HSP90 (Whitesell et al., 1994; Schulte and Neckers, 1998). Moreover, X-ray crystallographic studies have shown that geldanamycin competes at the ATP binding site and inhibits the intrinsic ATPase activity of HSP90 (Prodromou et al., 1997; Panaretou et al., 1998). This in turn prevents the formation of mature multimeric HSP90 complexes capable of chaperoning client proteins. As a result, the client proteins are targeted for degradation via the ubiquitin proteasome pathway. 17-Allylamino, 17-demethoxygeldanamycin (17AAG) retains the property of HSP90 inhibition resulting in client protein depletion and antitumour activity in cell culture and xenograft models (Schulte et al, 1998; Kelland et al, 1999), but has significantly less hepatotoxicity than geldanamycin (Page et al, 1997). 17AAG is currently being evaluated in Phase I clinical trials.

Radicicol is a macrocyclic antibiotic shown to reverse the malignant phenotype of v-Src and v-Ha-Ras transformed fibroblasts (Kwon et al, 1992; Zhao et al, 1995). It was shown to degrade a number of signalling proteins as a consequence of HSP90 inhibition (Schulte et al., 1998). X-ray crystallographic data confirmed that radicicol also binds to the N terminal domain of HSP90 and inhibits the intrinsic ATPase activity (Roe et al., 1998). Radicicol lacks antitumour activity in vivo due to the unstable chemical nature of the compound.

Coumarin antibiotics are known to bind to bacterial DNA gyrase at an ATP binding site homologous to that of the HSP90. The coumarin, novobiocin, was shown to bind to the carboxy terminus of HSP90, i.e., at a different site to that occupied by the benzoquinone ansamycins and radicicol which bind at the N-terminus (Marcu et al., 2000b). However, this still resulted in inhibition of HSP90 function and degradation of a number of HSP90-chaperoned signalling proteins (Marcu et al., 2000a). Geldanamcyin cannot bind HSP90 subsequent to novobiocin; this suggests that some interaction between the N and C terminal domains must exist and is consistent with the view that both sites are important for HSP90 chaperone properties.

A purine-based HSP90 inhibitor, PU3, has been shown to result in the degradation of signalling molecules, including erb-B2, and to cause cell cycle arrest and differentiation in breast cancer cells (Chiosis et al., 2001).

HSP90 as a Therapeutic Target

Due to its involvement in regulating a number of signalling pathways that are crucially important in driving the phenotype of a tumour, and the discovery that certain bioactive natural products exert their effects via HSP90 activity, the molecular chaperone HSP90 is currently being assessed as a new target for anticancer drug development (Neckers et al., 1999).

The predominant mechanism of action of geldanamycin, 17AAG, and radicicol involves binding to HSP90 at the ATP binding site located in the N-terminal domain of the protein, leading to inhibition of the intrinsic ATPase activity of HSP90 (see, e.g., Prodromou et al., 1997; Stebbins et al., 1997; Panaretou et al., 1998).

Inhibition of HSP90 ATPase activity prevents recruitment of co-chaperones and encourages the formation of a type of HSP90 heterocomplex from which these client proteins are targeted for degradation via the ubiquitin proteasome pathway (see, e.g., Neckers et al., 1999; Kelland et al., 1999).

Treatment with HSP90 inhibitors leads to selective degradation of important proteins involved in cell proliferation, cell cycle regulation and apoptosis, processes which are fundamentally important in cancer.

Inhibition of HSP90 function has been shown to cause selective degradation of important signalling proteins involved in cell proliferation, cell cycle regulation and apoptosis, processes which are fundamentally important and which are commonly deregulated in cancer (see, e.g., Hostein et al., 2001). An attractive rationale for developing drugs against this target for use in the clinic is that by simultaneously depleting proteins associated with the transformed phenotype, one may obtain a strong antitumour effect and achieve a therapeutic advantage against cancer versus normal cells. These events downstream of HSP90 inhibition are believed to be responsible for the antitumour activity of HSP90 inhibitors in cell culture and animal models (see, e.g., Schulte et al., 1998; Kelland et al., 1999).

BRIEF DESCRIPTION OF THE INVENTION

The present invention makes available a new class of substituted pyrazole compounds, which are HSP90 inhibitors and which inhibit cancer cell proliferation. Aromatic substitution on one ring carbon atom and non-aromatic carbocyclic or heterocyclic substitution on an adjacent ring carbon atom are principle characterising features of the compounds of the invention.

DETAILED DESCRIPTION OF THE INVENTION

According to the present invention there is provided a compound of formula (IA) or (IB) or a salt, N-oxide, hydrate or solvate thereof:

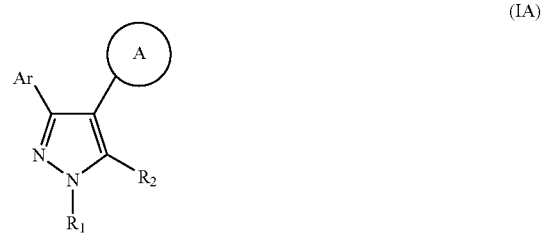

wherein
Ar is an aryl, aryl($C_1$-$C_6$ alkyl), heteroaryl, or heteroaryl($C_1$-$C_6$ alkyl) group, any of which being optionally substituted in the aryl or heteroaryl part thereof,
$R_1$ is hydrogen or optionally substituted $C_1$-$C_6$ alkyl;
$R_2$ is hydrogen, optionally substituted cycloalkyl, cycloalkenyl, $C_1$-$C_6$ alkyl, $C_1$-$C_6$ alkenyl, or $C_1$-$C_6$ alkynyl; or a carboxyl, carboxamide or carboxyl ester group; and;
ring A is a non aromatic carbocyclic or heterocyclic ring wherein (i) a ring carbon is optionally substituted, and/or (ii) a ring nitrogen is optionally substituted by a group of formula -(Alk$^1$)$_p$-(Cyc)$_n$-(Alk$^3$)$_m$-(Z)$_r$-(Alk$^2$)$_s$-Q where Alk$^1$, Alk$^2$ and Alk$^3$ are optionally substituted $C_1$-$C_3$ alkyl, Cyc is an optionally substituted carbocyclic or heterocyclic radical;
m, n, p, r and s are independently 0 or 1,
Z is —O—, —S—, —(C=O)—, —SO$_2$—, —C(=O)O—, —OC(=O)—, —NR$^A$—, —C(=O)NR$^A$—, —NR$^A$C(=O)—, —SO$_2$NR$^A$—, or —NR$^A$SO$_2$— wherein R$^A$ is hydrogen or $C_1$-$C_6$ alkyl, and Q is hydrogen or an optionally substituted carbocyclic or heterocyclic radical.

A subset of the compounds of the invention consists of those of formula (IA) or (IB) as defined above, wherein Ar is an optionally substituted aryl, or heteroaryl radical; and ring A is a non aromatic carbocyclic or heterocyclic ring wherein (i) a ring carbon is optionally substituted, and/or (ii) a ring nitrogen is optionally substituted by a group of formula $-(Alk^1)_p-(Z)_r-(Alk^2)_s-Q$ where $Alk^1$, $Alk^2$ are optionally substituted $C_1-C_3$ alkyl, p, r and s are independently 0 or 1, Z is —O—, —S—, —(C=O)—, —$SO_2$—, —C(=O)O—, —OC(=O)—, —$NR^A$—, —C(=O)$NR^A$—, —$NR^AC$(=O)—, —$SO_2NR^A$—, or —$NR^ASO_2$— wherein $R^A$ is hydrogen or $C_1-C_6$ alkyl, and Q is hydrogen or an optionally substituted carbocyclic or heterocyclic radical.

When $R_1$ in compounds IA and IB is hydrogen, then compounds IA and IB are tautomeric forms of the same compound.

As used herein:

the term "carboxyl group" refers to a group of formula —COOH;

the term "carboxyl ester group" refers to a group of formula —COOR, wherein R is a radical actually or notionally derived from the hydroxyl compound ROH; and the term "carboxamide group" refers to a group of formula —CONR$_a$R$_b$, wherein —NR$_a$R$_b$ is a primary or secondary (including cyclic) amino group actually or notionally derived from ammonia or the amine HNR$_a$R$_b$.

As used herein, the term "($C_1-C_6$)alkyl" refers to a straight or branched chain alkyl radical having from 1 to 6 carbon atoms, including for example, methyl, ethyl, n-propyl, isopropyl, n-butyl, isobutyl, sec-butyl, t-butyl, n-pentyl and n-hexyl.

As used herein, the term "($C_1-C_6$)alkenyl" refers to a straight or branched chain alkenyl radical having from 2 to 6 carbon atoms and containing at least one double bond of E or Z configuration, including for example, ethenyl and allyl.

As used herein, the term "($C_1-C_6$)alkynyl" refers to a straight or branched chain alkenyl radical having from 2 to 6 carbon atoms and containing at least one triple bond, including for example, ethynyl and prop-2-ynyl.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "aryl" refers to a mono-, bi- or tri-cyclic carbocyclic aromatic radical. Illustrative of such radicals are phenyl, biphenyl and napthyl.

As used herein the term "carbocyclic" refers to a cyclic ring or ring system whose ring atoms are all carbon, and includes monocyclic aryl, cycloalkyl and cycloalkenyl radicals.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic aromatic or non-aromatic radical containing one or more heteroatoms selected from S, N and O, and to groups consisting of a monocyclic aromatic or non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four substituents, each of which independently may be, for example, ($C_1-C_6$)alkyl, ($C_1-C_6$)alkoxy, hydroxy, hydroxy($C_1-C_6$)alkyl, mercapto, mercapto($C_1-C_6$)alkyl, ($C_1-C_6$)alkylthio, halo (including fluoro and chloro), trifluoromethyl, trifluoromethoxy, nitro, nitrile (—CN), oxo, phenyl, —COOH, —COOR$^A$, —COR$^A$, —$SO_2R^A$, —$CONH_2$, —$CONHNH_2$, —CONHNHR$^A$, —CONHNR$^A$R$^B$, —$SO_2NH_2$, —CONHR$^A$, —$SO_2NHR^A$, —CONR$^A$R$^B$, —$SO_2NR^AR^B$, —$NH_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein $R^A$ and $R^B$ are independently a ($C_1-C_6$) alkyl group.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

Some compounds of the invention contain one or more actual or potential chiral centres because of the presence of asymmetric carbon atoms. The presence of several asymmetric carbon atoms gives rise to a number of diastereoisomers with R or S stereochemistry at each chiral centre. The invention includes all such diastereoisomers and mixtures thereof.

In the compounds of the invention:

Ar is preferably a 2-hydroxyphenyl group, more preferably a 2,4-dihydroxyphenyl group, which is optionally further substituted, for example in the 5-position. Optional substituents include for example, chloro or bromo, optionally substituted phenyl or $C_1-C_6$ alkyl, and phenylethyl which is optionally substituted in the phenyl ring thereof.

$R_1$ and $R_2$ may be, for example, hydrogen, methyl, ethyl, n- or iso-propyl, or hydroxyethyl. Hydrogen is presently preferred in the case of $R_1$, and hydrogen or methyl is presently preferred in the case of $R_2$;

Ring A may be, for example, a ring of formula (IIA) or (IIB):

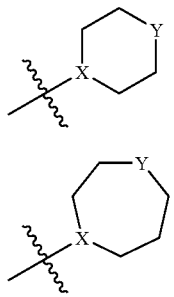

(IIA)

(IIB)

wherein X represents CH or N, and Y represents CH, O, or NH, wherein (i) a ring carbon is optionally substituted, and/or (ii) a ring nitrogen is optionally substituted by a group of formula -(Alk$^1$)$_p$-(Cyc)$_n$-(Alk$^3$)$_m$-(Z)$_r$-(Alk$^2$)$_s$-Q where Alk$^1$, Alk$^2$ and Alk$^3$ are optionally substituted C$_1$-C$_3$ alkyl, Cyc is an optionally substituted carbocyclic or heterocyclic radical;

m, n, p, r and s are independently 0 or 1,

Z is —O—, —S—, —(C═O)—, —SO$_2$—, —C(═O)O—, —C(═O)NR$^A$—, —SO$_2$NR$^A$—, —NR$^A$C(═O)—, —NR$^A$SO$_2$— or —NR$^A$— wherein R$^A$ is hydrogen or C$_1$-C$_6$ alkyl, and Q is hydrogen or an optionally substituted carbocyclic or heterocyclic radical.

When the optionally substituted ring A is of formula (IIA), X is preferably N and Y is NH or CH, and more preferably X is N, and Y is —NR$^A$— wherein R$^A$ is a radical of formula -(Alk$^1$)-Q, wherein Alk$^1$ is a C$_1$-C$_3$ alkylene radical. For example in such cases R$^A$ may be an optionally substituted benzyl group and Q may be optionally substituted phenyl, pyridyl, furyl, thienyl, oxadiazolyl, imidazolyl or morpholinyl.

Alternatively, when the optionally substituted ring A is of formula (IIA), X may be and Y may be —NR$^A$— wherein R$^A$ is a radical of formula -(Alk$^1$)$_p$-(Cyc)$_n$-(Alk$^3$)$_m$-(Z)$_r$-(Alk$^2$)$_s$-Q. In one of many such cases, p is 1 and m are each 1, and Cyc is a phenylene radical.

In cases when the optionally substituted ring A is of formula (IIA), X is N and Y is —NR$^A$— specicic examples of substitutents R$^A$ are to be found in compounds of the Examples herein.

A presently preferred class of compounds of the invention consists of those of formula (IC) or (ID) or a salts, N-oxides, hydrates or solvates thereof:

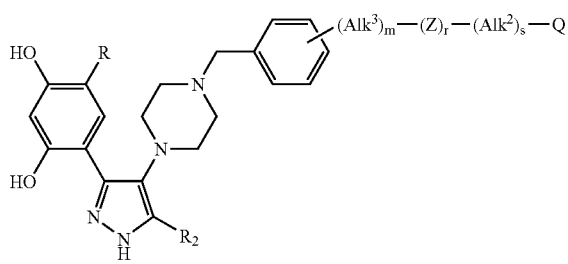

(IC)

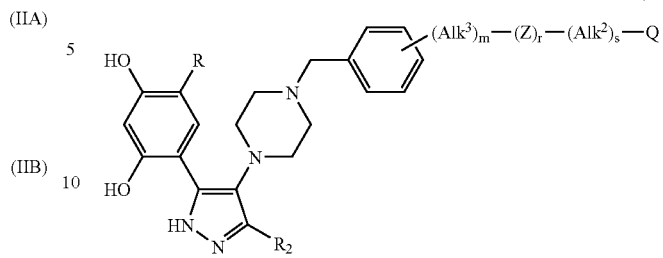

(ID)

wherein R is hydrogen, an optional substituent, or a phenylethyl group which is optionally substituted in the phenyl ring, and R$_2$, m, r, s, Alk$^3$, Z and Alk$^2$ are as defined above. In such compounds R$_2$ may be hydrogen, R may be, for example chloro, bromo, or a phenylethyl group which is optionally substituted in the phenyl ring, and n may be is 0, r may be 1, and Z may be —C(═O)NH—.

Specific compounds of the invention include those of the Examples herein

Compounds of the invention may be prepared by methods analogous to those used in the Examples herein, and in general are accessible by reaction of a compound of formula (IIA) with a compound of formula (IIB)

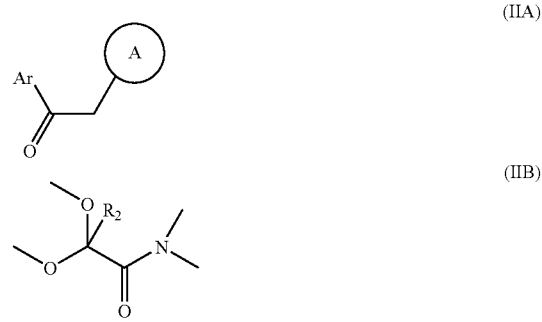

(IIA)

(IIB)

to form an intermediate compound of formula (IIC)

(IIC)

which is then reacted with the hydrazine H$_2$N—NHR$_1$ to form a mixture of the two pyrazole compounds (1A) and (IB), which may then be then separated. Of course it may be desirable to protect any potentially reactive groups in Ar, ring A and the substituents R1 and R2 during the above reactions and to remove the protecting groups subsequently.

Compounds of formula (IIA) may be prepared by nucleophilic displacement of bromine from a compound of formula (III) by an anion of ring A:

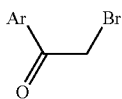

(III)

Some compounds of the invention are accessible by chemical modification of other compounds of the invention made by the above general method.

The compounds of the invention are inhibitors of HSP90 and are thus useful in the treatment of diseases which are responsive to inhibition of HSP90 activity such as cancers; viral diseases such as Hepatitis C (HCV) (Waxman, 2002); Immunosupression such as in transplantation (Bijlmakers, 2000 and Yorgin, 2000); Anti-inflammatory diseases (Bucci, 2000) such as Rheumatoid arthritis, Asthma, MS, Type I Diabetes, Lupus, Psoriasis and Inflammatory Bowel Disease; Cystic fibrosis (Fuller, 2000); Angiogenesis-related diseases (Hur, 2002 and Kurebayashi, 2001): diabetic retinopathy, haemangiomas, psoriasis, endometriosis and tumour angiogenesis. Also an Hsp90 inhibitor of the invention may protect normal cells against chemotherapy-induced toxicity and be useful in diseases where failure to undergo apoptosis is an underlying factor. Such an Hsp90 inhibitor may also be useful in diseases where the induction of a cell stress or heat shock protein response could be beneficial, for example, protection from hypoxia-ischemic injury due to elevation of Hsp70 in the heart (Hutter, 1996 and Trost, 1998) and brain (Plumier, 1997 and Rajder, 2000). An Hsp90 inhibitor could also be useful in diseases where protein misfolding or aggregation is a major causal factor, for example, scrapie/CJD, Huntingdon's and Alzheimer's (Sittler, 2001; Trazelt, 1995 and Winklhofer, 2001).

Accordingly, the invention also provides:
(i) a method of treatment of diseases or conditions responsive to inhibition of HSP90 activity in mammals, in particular in humans, which method comprises administering to the mammal an effective amount of a compound of formula (IA) or (IB) above; and
(ii) a compound of formula (IA) or (IB) above, for use in human or veterinary medicine, particularly in the treatment of diseases or conditions responsive to inhibition of HSP90 actvity; and
(iii) the use of a compound of formula (IA) or (IB) above in the preparation of an agent for the management (by which is meant treatment or prophylaxis) of diseases or conditions responsive to inhibition of HSP90 activity.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl Phydroxybenzoate or sorbic acid, and if desired conventional flavouring or colourng agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples illustrate the preparation and activities of specific compounds of the invention.

EXAMPLE 1

4-[3-(5-Chloro-2,4-dihydroxy-phenyl)-1H-pyrazol-4-yl]-piperazine-1-carboxylic acid tert-butyl ester, and

EXAMPLE 2

4Chloro-6-(4-piperazin-1-yl-1H-pyrazol-3-yl)-benzene-1,3-diol

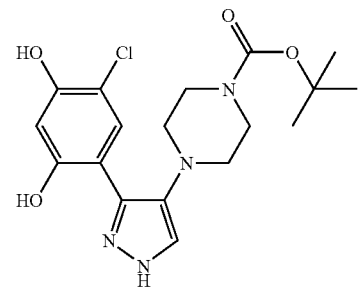

Example 1

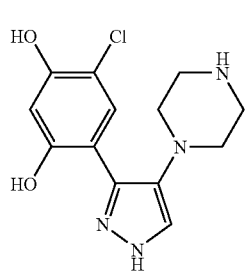

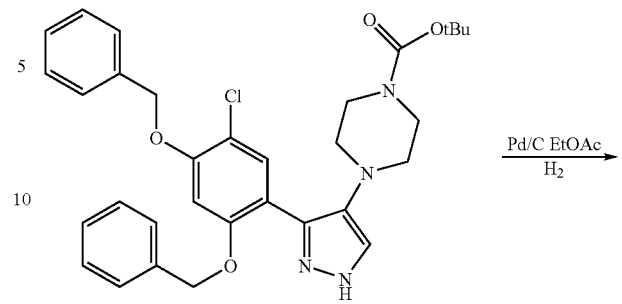

Example 2

Scheme 1: Synthesis of piperazinopyrazoles.

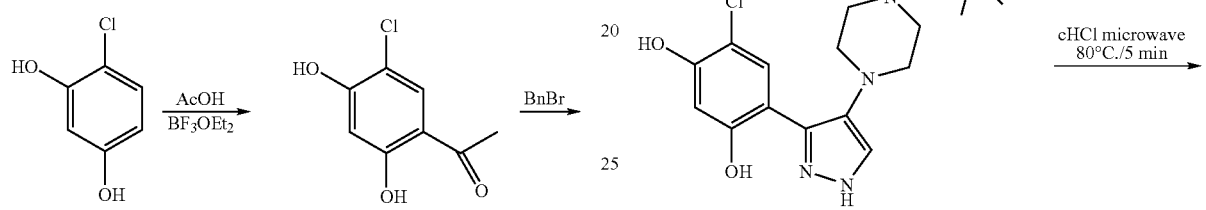

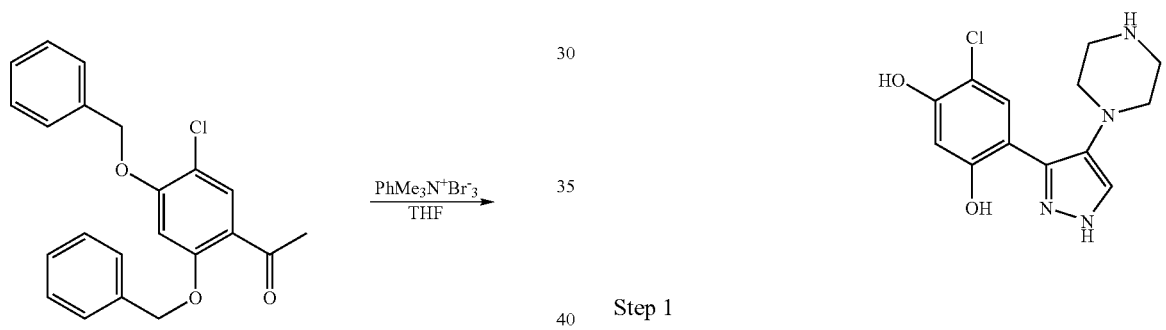

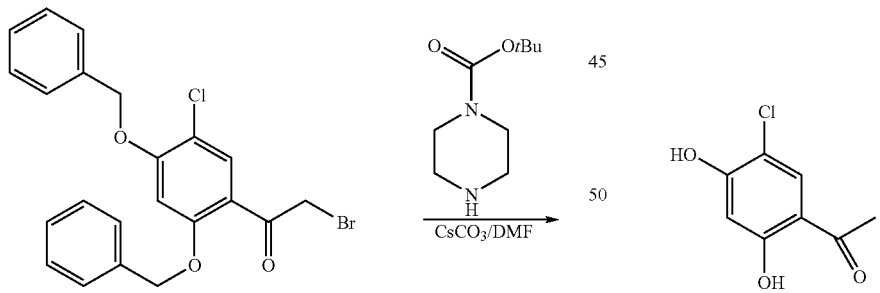

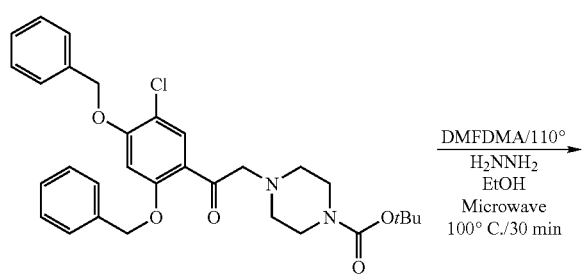

Step 1

1-(5-Chloro-2,4-dihydroxy-phenyl)-ethanone

Acetic acid (17.5 mL) was added dropwise to a suspension of 4-chlororesorcinol (42.5 g, 0.293 mmol) in boron trifluoride etherate (200 mL) under a nitrogen atmosphere. The reaction mixture was heated at 90° C. for 3.5 hours and then allowed to cool to room temperature. A solid had formed after around 1 hour of cooling. The mixture was poured into 700 mL of a 10% w/v aqueous sodium acetate solution. This mixture was stirred vigorously for 2.5 hours. A light brown solid had formed which was filtered, washed with water and air-dried overnight to afford 1-(5-chloro-2,4-dihydroxy-phenyl)-ethanone (31.6 g, 58%). LCMS: [M−H]$^+$ 185.

Step 2

1-(2,4-Bis-benzyloxy-5-chloro-phenyl)-ethanone

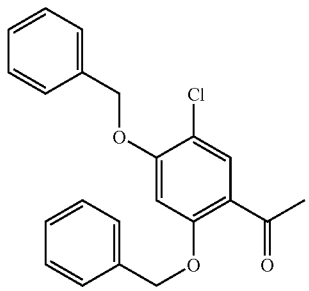

Benzyl bromide (30 mL) was added to a mixture of 1-(5-chloro-2,4-dihydroxy-phenyl)-ethanone (20 g, 0.107 moles) and potassium carbonate (37 g, 2.5 equiv) in acetonitrile (350 mL). The mixture was heated at reflux for 6 hours then allowed to cool and stirred overnight. The mixture was filtered and the solids were washed with dichloromethane (3×100 mL). The combined organic extracts were evaporated in vacuo to leave a pale yellow solid which was triturated with a mixture of hexane (350 mL)/ethyl acetate (15 mL) and filtered to give an off-white solid, 1-(2,4-bis-benzyloxy-5-chloro-phenyl)-ethanone (35.4 g, 90%). 1H NMR (400 MHz) consistent with structure.

Step 3

1-(2,4-Bis-benzyloxy-5-chloro-phenyl)-2-bromo-ethanone

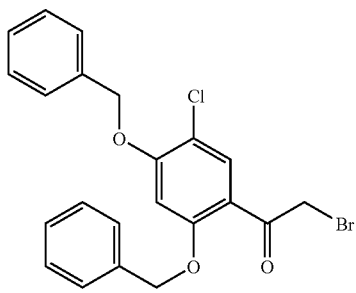

Phenyltrimethylammonium tribromide (7.5 g, 0.02 mol) was added portionwise to a stirred solution of 1-(2,4-Bis-benzyloxy-5-chloro-phenyl)-ethanone (7.09 g, 0.019 mol) in tetrahydrofuran (100 ml) and the mixture was stirred for 2 h. The mixture was partitioned between water (100 ml) and diethyl ether (2×50 ml). The combined organic phases were dried over magnesium sulphate and concentrated to give a beige solid. Crystallisation from toluene (100 ml) gave 1-(2,4-Bis-benzyloxy-5-chloro-phenyl)-2-bromo-ethanone as a white solid (4.5 g)

LC retention time 2.97 minutes, no ion (Run time 3.75 min)

Step 4

4-[2-(2,4-Bis-benzyloxy-5-chloro-phenyl)-2-oxo-ethyl]-piperazine-1-carboxylic acid tert-butyl ester

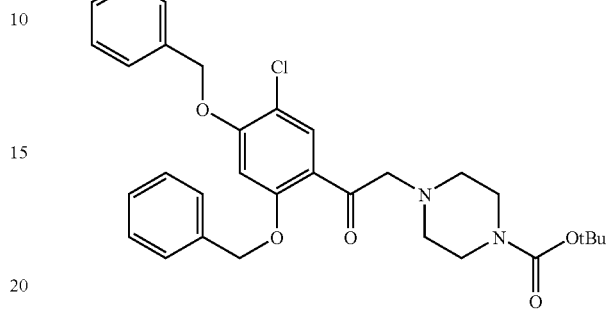

Cesium carbonate (2.95 g, 9 mmol) was added in three portions to a stirred solution of 1-(2,4-Bis-benzyloxy-5-chloro-phenyl)-2-bromo-ethanone (4.4 g, 9 mmol) and piperazine-1-carboxylic acid tert-butyl ester (1.74 g, 9 mmol) in dimethylformamide (20 ml). The suspension was stirred for 2 h then partitioned between water (200 ml) and ethyl acetate (3×50 ml). The combined organic extracts were washed with water (100 ml), dried over magnesium sulphate and concentrated to give 4-[2-(2,4-Bis-benzyloxy-5-chloro-phenyl)-2-oxo-ethyl]-piperazine-1-carboxylic acid tert-butyl ester as a yellow oil (4 g)

LC retention time 2.53 minutes $[M+H]^+$ 551.5 (Run time 3.75 min)

Step 5

4-[3-(2,4-Bis-benzyloxy-5-chloro-phenyl)-1H-pyrazol-4-yl]-piperazine-1-carboxylic acid tert-butyl ester

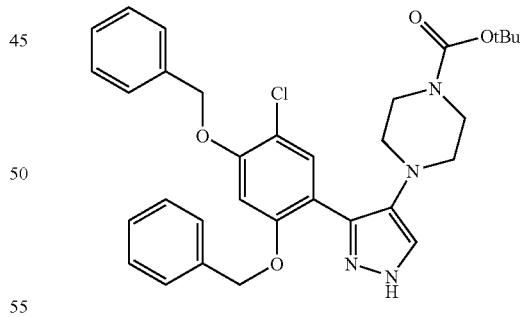

A solution of 4-[2-(2,4-Bis-benzyloxy-5-chloro-phenyl)2-oxo-ethyl]-piperazine-1-carboxylic acid tert-butyl ester (2 g, 3.6 mmol) in dimethylformamide dimethylacetal (4 ml) was heated at reflux for 3 h. A further quantity of dimethylformamide dimethylacetal (15 ml) was added, and the mixture was heated at reflux for 4 h. The mixture was split into 7 microwave vessels. Ethanol (1 ml) and hydrazine hydrate (1 ml) was added to each microwave vessel, and each was heated at 120° C. for 5 minutes. The contents of all the vessels were combined and partitioned between water (50 ml) and dichloromethane (3×30 ml). The combined organic phases were concentrated and purified on a bond elute cartridge (20 g) eluting with hexane, followed by hexane:ether; 4:1 then 1:1 then 1:2 then 1:4 gave 4-[3-(2,4-Bis-benzyloxy-5-chloro-phenyl)-1H-pyrazol-4-yl]-piperazine-1-carboxylic acid tert-butyl ester as a white solid (620 mg)

LC retention time 2.98 minutes [M+H]+ 575.5 (Run time 3.75 min)

Step 6

4-[3-(5-Chloro-2,4-dihydroxy-phenyl)-1H-pyrazol-4-yl]-piperazine-1-carboxylic acid tert-butyl ester (Example 1)

A solution of 4-[3-(2,4-Bis-benzyloxy-5-chloro-phenyl)-1H-pyrazol-4-yl]-piperazine-1-carboxylic acid tert-butyl ester (230 mg, 0.4 mmol) in ethyl acetate (15 ml) was hydrogenated over 10% palladium on carbon for 1.5 h. The suspension was filtered through celite, washing with dichloromethane:ethanol (1:1). The filtrate was concentrated to leave 4-[3-(5-chloro-2,4-dihydroxy-phenyl)-1H-pyrazol-4-yl]-piperazine-1-carboxylic acid tert-butyl ester (Example 1) as a white solid (72 mg)

LC retention time 2.24 minutes [M+H]+ 395.3 (Run time 3.75 min)

Step 7

4-Chloro-6-(4-piperazin-1-yl-1H-pyrazol-3-yl)-benzene-1,3-diol (Example 2)

Method A

A mixture of 4-[3-(2,4-Bis-benzyloxy-5-chloro-phenyl)-1H-pyrazol-4-yl]-piperazine-1-carboxylic acid tert-butyl ester (25 mg, 0.06 mmol) and concentrated hydrochloric acid (1 ml) was heated in the microwave at 80° C. for 5 min. The mixture was evaporated to dryness, azeotroping with toluene to give 4-chloro-6-(4-piperazin-1-yl-1H-pyrazol-3-yl)-benzene-1,3-diol (10 mg) (Example 2)

LC retention time 1.37 minutes [M+H]+ 295.2 (Run time 3.75 min)

Method B

Boron trichloride (1M solution in dichloromethane; 8 ml, 8 mmol) was added dropwise to a solution of 4-[3-(2,4-Bis-benzyloxy-5-chloro-phenyl)-1H-pyrazol-4-yl]-piperazine-1-carboxylic acid tert-butyl ester (1.5 g, 2.6 mmol) in dichloromethane (15 ml) at 0° C. The resulting mixture was stirred at room temperature for 1 h, then basified with saturated sodium bicarbonate solution. The suspension was concentrated in vacuo, azeotroping with toluene until the residue was dry. The residue was triturated with dichloromethane:ethanol (1:1; 15 ml) and filtered. The filtrate was purified on a bond elute cartridge (20 g) eluting with dichloromethane:ethanol:ammonia, 50:8:1 then 20:8:1 to give 4-chloro-6-(4-piperazin-1-yl-1H-pyrazol-3-yl)-benzene-1,3-diol as a pale yellow solid (400 mg) (Example 2)

LC retention time 1.37 minutes [M+H]+ 295.2 (Run time 3.75 min)

The compound of Example 1 had activity 'B' in the ATPase assay described below, and the compound of Example 2 had activity 'A'

The compounds in the following table were prepared as described in scheme 1 using the corresponding amine, and were purified using HPLC The entries in the column "Hsp90 IC50" are the results obtained in the ATPase assay described below.

| Example | Structure | MH+ | Hsp90 IC50 |
|---|---|---|---|
| 3 | 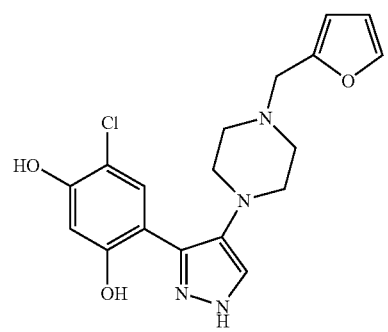 | 296 | B |
| 4 | 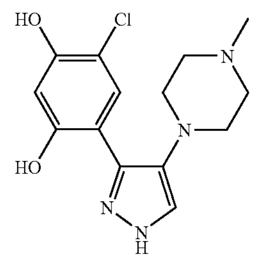 | 309 | A |

EXAMPLE 5

4-Chloro-6-[4-(4-furan-2-ylmethyl-piperazin-1-yl)-1H-pyrazol-3-yl]-benzene-1,3-diol this compound was made by the route summarised in Scheme 2:

Scheme 2: Reductive aminations of piperazines.

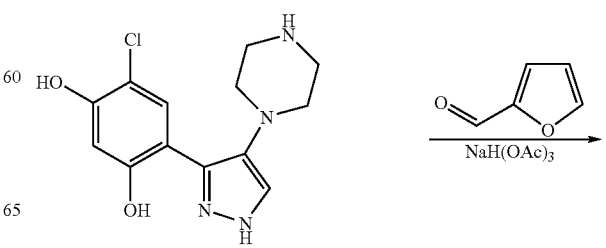

-continued

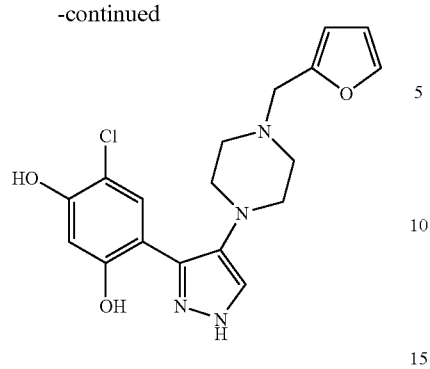

Sodium triacetoxyborohydride (150 mg, 0.7 mmol) was added in one portion to a mixture of 4-chloro-6-(4-piperazin-1-yl-1H-pyrazol-3-yl)-benzene-1,3-diol (43 mg, 0.146 mmol), furfuraldehyde (0.025 ml, 0.3 mmol), acetic acid (0.5 ml) and dichloromethane (1 ml). Stirring under nitrogen was continued for 3 h, and the reaction mixture was partitioned between water (10 ml) and dichloromethane (3×10 ml). The combined organic phases were dried over magnesium sulphate and concentrated and purified on a bond elute cartridge (5 g) eluting with dichloromethane:ethanol:ammonia (100:8:1) gave 4-chloro-6-[(4-(4-furan-2-ylmethyl-piperazin-1-yl)-1H-pyrazol-3-yl]-benzene-1,3-diol as a white solid (10 mg).

LC retention time 1.68 minutes $[M+H]^+$ 375.3 (Run time 3.75 min)

The compound of Example 5 had activity 'B' in the ATPase assay described below.

The compounds of Examples 6 and 7 were also prepared according to Scheme 2 using acetaldehyde and 3-pyridyl aldehyde, respectively. The entries in the column "Hsp90 IC50" are the results obtained in the ATPase assay described below.

| Example | Structure | MH+ | Hsp90 IC50 |
|---|---|---|---|
| 6 | 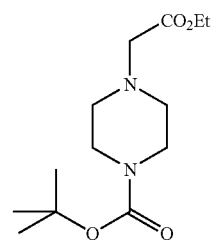 | 323 | A |
| 7 | 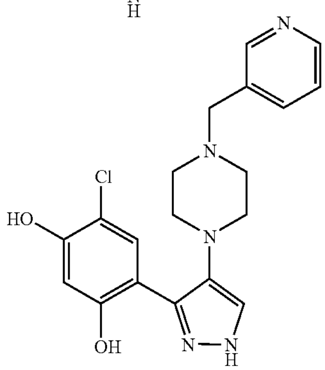 | 386 | A |

EXAMPLE 8

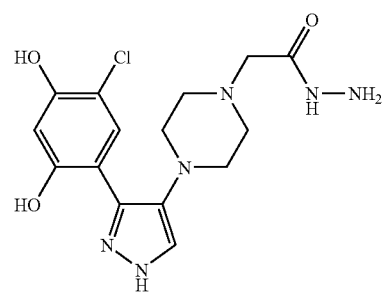

The compound of Example 8 was prepared as described in the following 2 schemes:

Scheme 3: Synthesis of piperazine acetic acid ethyl ester.

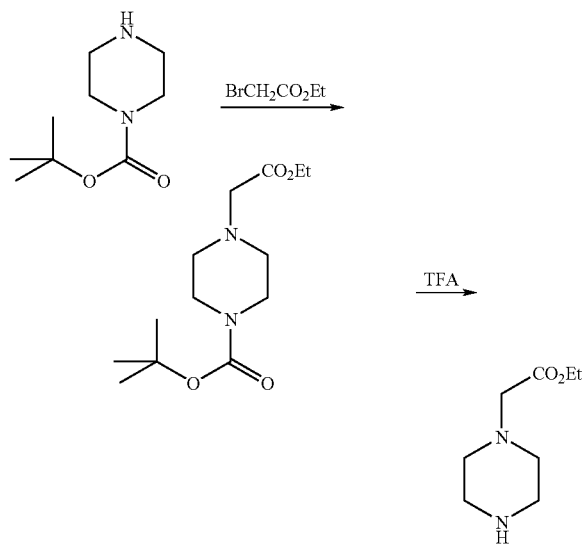

Step 1

4-Ethoxycarbonylmethyl-piperazine-1-carboxylic acid tert-butyl ester

Piperazine-1-carboxylic acid tert-butyl ester (2.62 g, 14 mmol), cesium carbonate (5 g, 15 mmol) and ethyl bromoacetate (1.56 ml, 14 mmol) was stirred at room temperature for 1 h. The mixture was partitioned between water (200 ml) and diethyl ether (2×100 ml). The combined organic phases were dried over magnesium sulphate and concentrated to give a yellow oil which crystallised to give 4-ethoxycarbonylmethyl-piperazine-1-carboxylic acid tert-butyl ester as a pale yellow solid (2.6 g)

$^1$H N.M.R (CDCl$_3$) δ=1.24 (3H, t, J=7.1 Hz), 1.43 (9H, s), 2.49 (4H, t, J=5 Hz), 3.20 (2H, s), 3.44 (4H, t, J=4.8 Hz), 4.16 (2H, q, J=7.1 Hz).

Step 2

Piperazin-1-yl-acetic acid ethyl ester

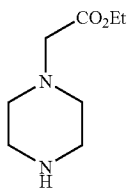

A solution of 4-ethoxycarbonylmethyl-piperazine-1-carboxylic acid tert-butyl ester in 90% trifluroacetic acid (5 ml) was stirred for 3 h. The mixture was basified with saturated sodium bicarbonate solution and concentrated. The residue was triturated with ethylacetate (30 ml) and filtered. The filtrate was concentrated to leave piperazin-1-yl-acetic acid ethyl ester as a yellow oil (ca 1.5 g)

$^1$H N.M.R (CDCl$_3$) δ=1.18 (3H, t, J=7.1 Hz), 2.40 (4H, t, J=4.1 Hz), 2.70 (4H, t, J=4.5 Hz), 3.13 (2H, s), 3.45 (1H, br s), 4.01 (2H, q, J=7.1 Hz)

Scheme 4: Synthesis of acyl hydrazide

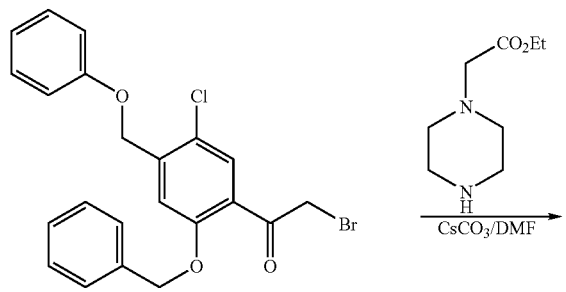

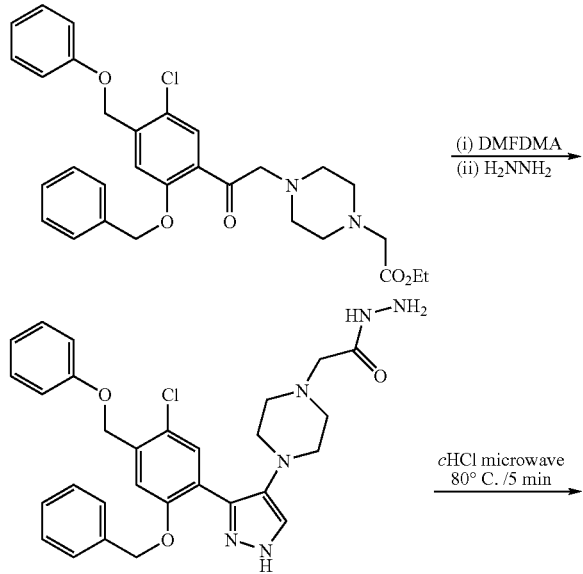

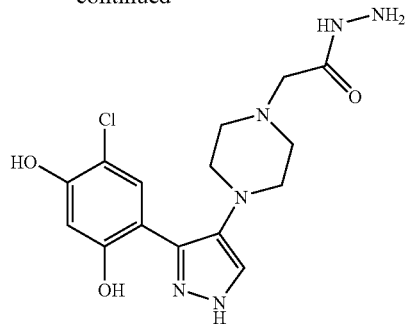

Step 3

{4-[2-(2,4-Bis-benzyloxy-5-chloro-phenyl)-2-oxo-ethyl]-piperazin-1-yl}-acetic acid ethyl ester

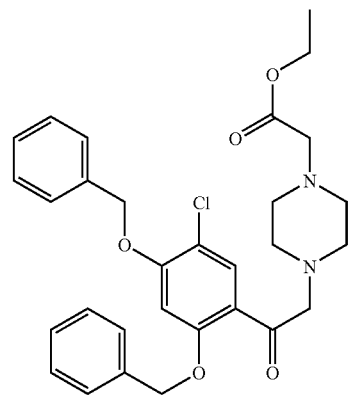

Prepared as described in Scheme 1 using piperazin-1-yl-acetic acid ethyl ester

LC retention time 2.32 minutes [M+H]$^+$ 537.5 (Run time 3.75 min)

Step 4

{4-[3-(2,4-Bis-benzyloxy-5-chloro-phenyl)-1H-pyrazol-4-yl]-piperazin-1-yl}-acetic acid ethyl ester and {4-[3-(2,4-Bis-benzyloxy-5-chloro-phenyl)-1H-pyrazol-yl]-piperazin-1-yl}-acetic acid hydrazide

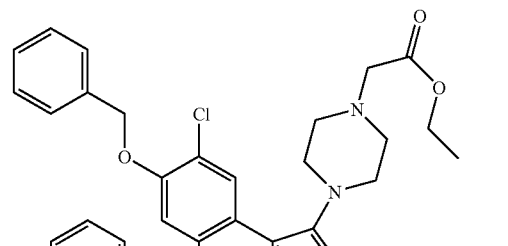

-continued

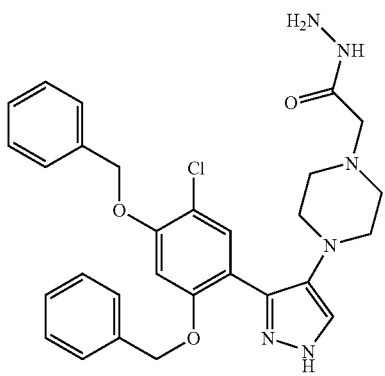

A solution of {4-[2-(2,4-Bis-benzyloxy-5-chloro-phenyl)-2-oxo-ethyl]-piperazin-1-yl}-acetic acid ethyl ester (1.5 g, 2.80 mmol) in dimethylforamide dimethylacetal (4 ml) was heated at 140° C. in the microwave for 30 min. The solution was split into two portions and each was mixed with hydrazine hydrate (0.1 ml) and ethanol (2 ml) and heated in the microwave at 100° C. for 5 min. The combined mixture was concentrated and purified on a bond elute cartridge to give {4-[3-(2,4-Bis-benzyloxy-5-chloro-phenyl)-1H-pyrazol-4-yl]-piperazin-1-yl}-acetic acid ethyl ester (230 mg) and {4-[3-(2,4-Bis-benzyloxy-5-chloro-phenyl)-1H-pyrazol-4-yl]-piperazin-1-yl}-acetic acid hydrazide (150 mg).

Step 5

{4-[3-(5-Chloro-2,4-dihydroxy-phenyl)-1H-pyrazol-4-yl]-piperazin-1-yl}-acetic acid hydrazide (Example 8)

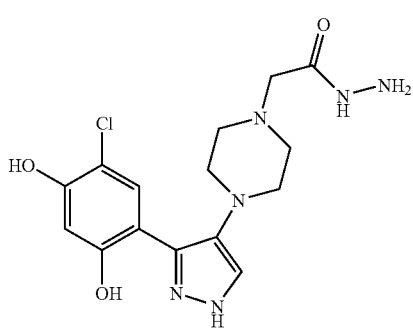

Prepared from {4-[3-(2,4-Bis-benzyloxy-5-chloro-phenyl)1H-pyrazol-4-yl]-piperazin-1-yl}-acetic acid hydrazide, analogously to Example 2, Step 7, Method A LC retention time 1.40 minutes [M+H]$^+$ 367.3 (Run time 3.75 min)

The compound of Example 8 had activity 'B' in the ATPase assay.

EXAMPLE 9

4-Chloro-6-{4-[4-(2-hydroxy-ethyl)-piperazin-1-yl]-1H-pyrazol-3-yl}-benzene-1,3-diol Scheme 5: Alkylation of piperazines:

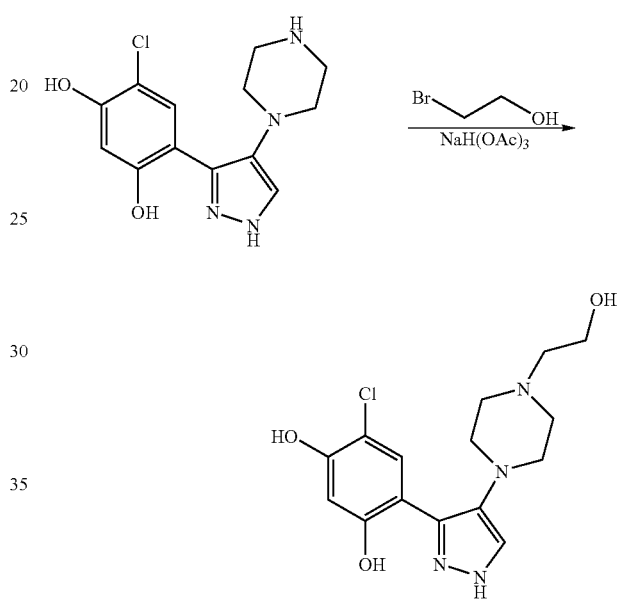

A mixture of 4-chloro-6-(4-piperazin-1-yl-1H-pyrazol-3-yl)-benzene-1,3-diol (43 mg, 0.146 mmol), cesium carbonate (48 mg, 0.146 mmol), 2-bromoethanol (0.025 ml, 0.35 mmol) and dimethylformamide (1 ml) was stirred at room temperature for 3 days. The mixture was evaporated to dryness and applied to a bond elute cartridge (5 g) with dichloromethane:methanol (49:1), then eluting with dichloromethane followed by dichloromethane:ethanol:ammonia (50:8:1 then 20:8:1) gave 4-chloro-6-{4-[4-(2-hydroxy-ethyl)-piperazin-1-yl]-1H-pyrazol-3-yl}-benzene-1,3-diol as a white solid (10 mg)

LC retention time 1.36 minutes [M+H]$^+$ 339.3 (Run time 3.75 min)

The compound of Example 9 had activity 'B' in the ATPase assay.

Examples 10 to 48 were prepared by the method summarised in Scheme 5, using the appropriate alkylating, acylating or sulfonylating agent. The entries in the column "Hsp90 IC50" are the results obtained in the ATPase assay or, where indicated by an asterisk, in the Fluorescence Polarisation (FP) assay described below:

| Example | Structure | MH+ | Hsp90 IC50 |
|---|---|---|---|
| 10 | 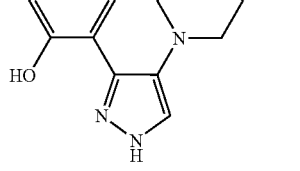 | 334 | B |
| 11 | 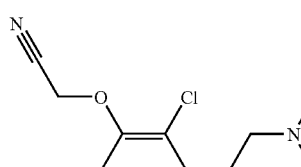 | 373 | B |
| 12 | 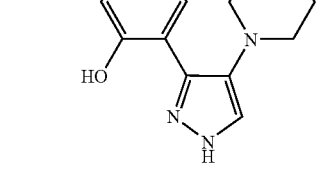 | 463 | A |
| 13 | 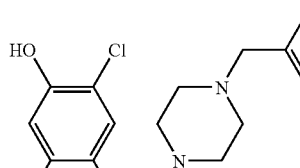 | 361 | A |
| 14 | 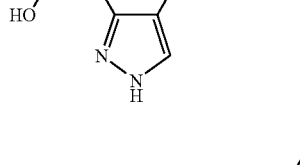 | 353 | A |

-continued
| Example | Structure | MH+ | Hsp90 IC50 |
|---|---|---|---|
| 15 | 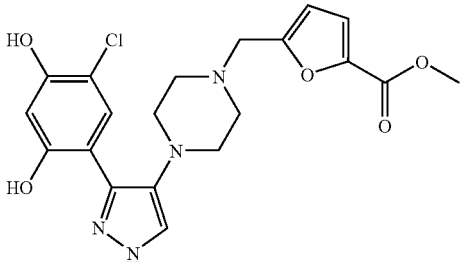 | 434 | A |
| 16 | 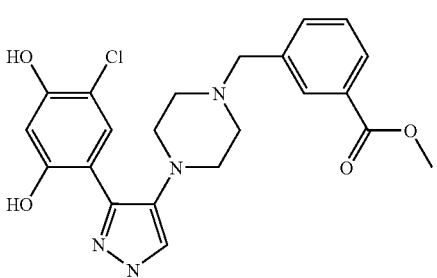 | 444 | A |
| 17 | 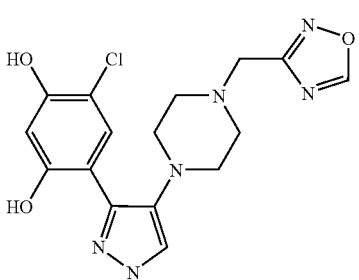 | 378 | A |
| 18 | 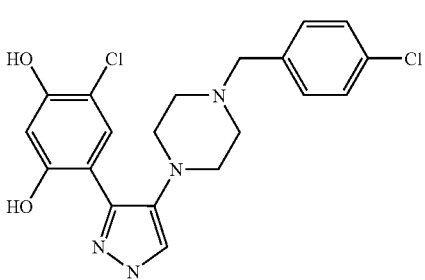 | 420 | A |
| 19 | 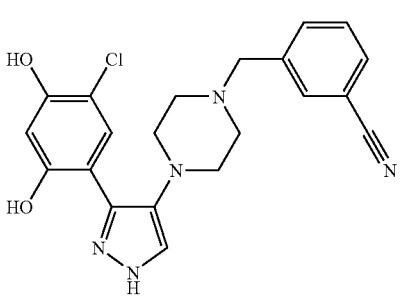 | 411 | A |

-continued

| Example | Structure | MH+ | Hsp90 IC50 |
|---|---|---|---|
| 20 | 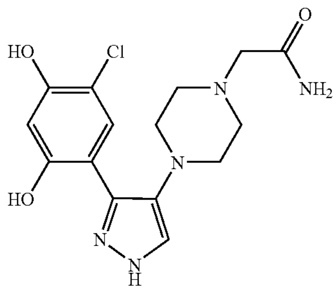 | 353 | A |
| 21 | 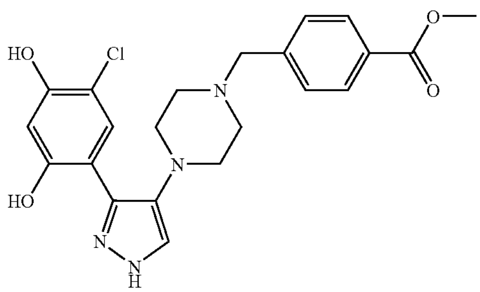 | 444 | A |
| 22 | 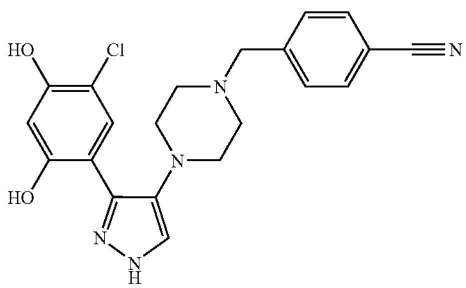 | 411 | A |
| 23 | 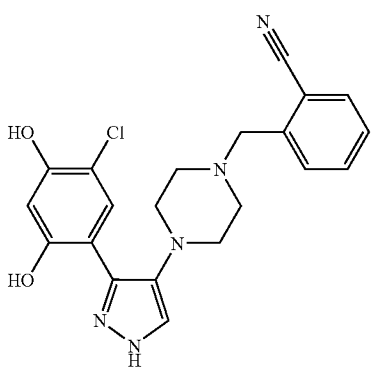 | 411 | A |
| 24 | 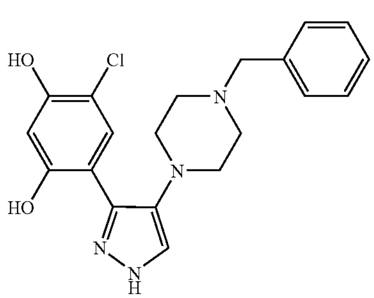 | 386 | A |

-continued

| Example | Structure | MH+ | Hsp90 IC50 |
|---|---|---|---|
| 25 | 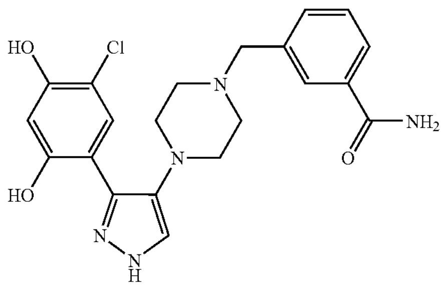 | 429 | A |
| 26 | 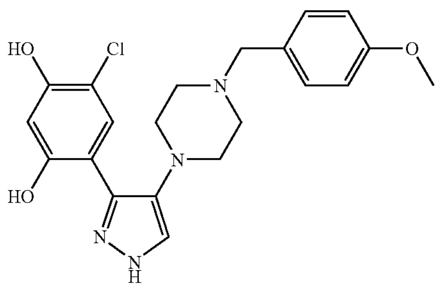 | 416 | A |
| 27 | 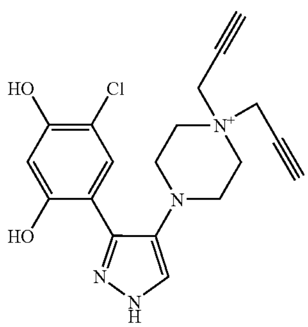 | 373 | A |
| 28 | 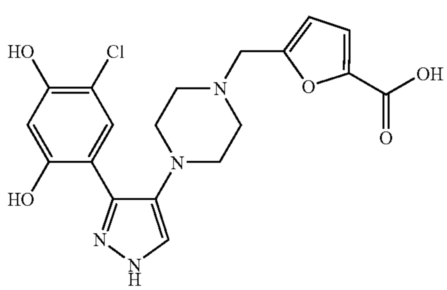 | 420 | A |
| 29 | 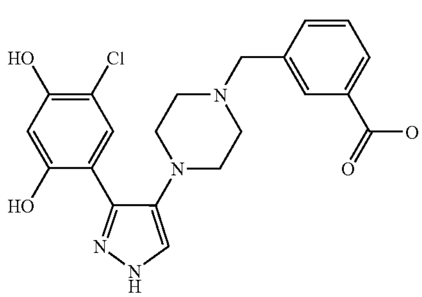 | 430 | A |

-continued

| Example | Structure | MH+ | Hsp90 IC50 |
|---|---|---|---|
| 30 | 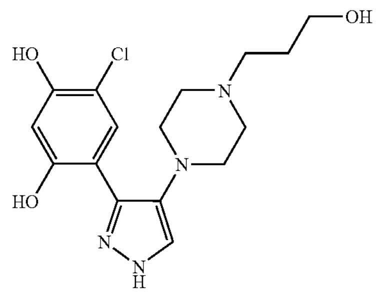 | 354 | A |
| 31 | 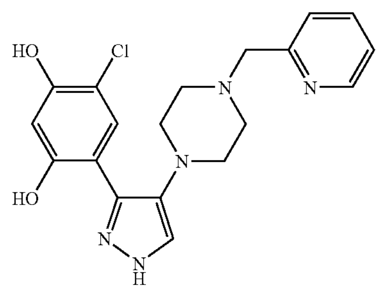 | 387 | A |
| 32 | 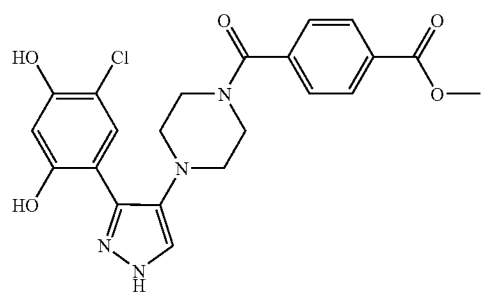 | 458 | B |
| 33 | 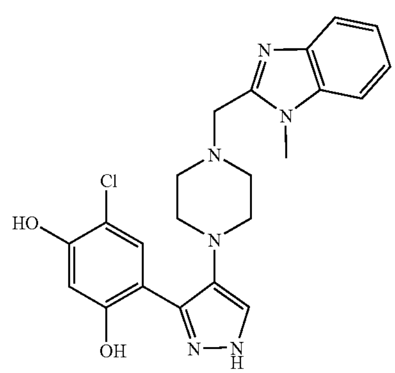 | 439 | B |
| 34 | 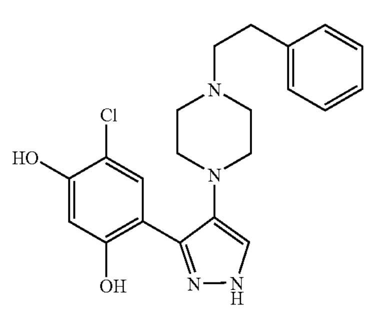 | 399 | A |

-continued

| Example | Structure | MH+ | Hsp90 IC50 |
|---|---|---|---|
| 35 | (structure) | 429 | A |
| 36 | (structure) | 428 | A |
| 37 | (structure) | 509 | A |
| 38 | (structure) | 469 | A |
| 39 | (structure) | 451 | A |

-continued
| Example | Structure | MH+ | Hsp90 IC50 |
|---|---|---|---|
| 40 | 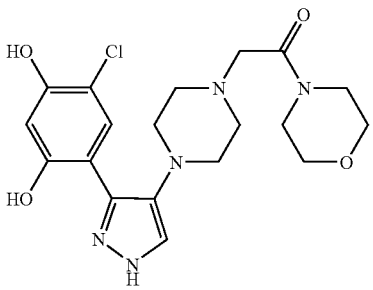 | 422 | A |
| 41 | 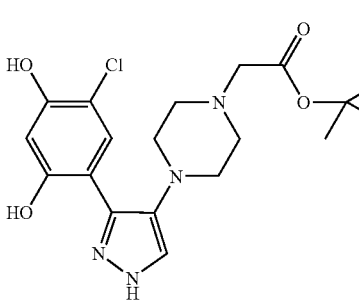 | 409 | B |
| 42 | 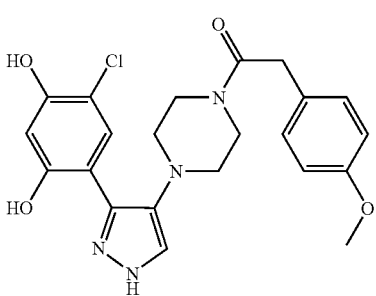 | 442 | B* |
| 43 | 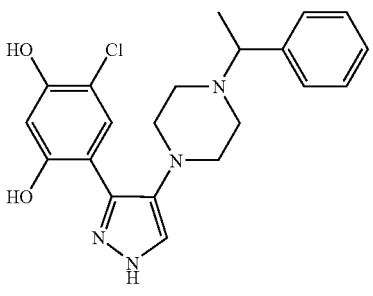 | 399 | A |
| 44 | 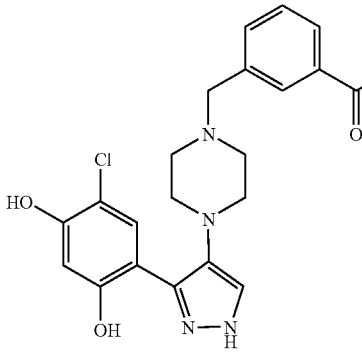 | 442 | A* |

-continued
| Example | Structure | MH+ | Hsp90 IC50 |
|---|---|---|---|
| 45 | 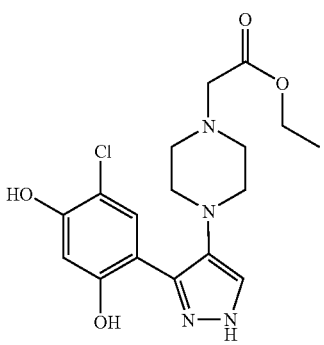 | 381 | A* |
| 46 | 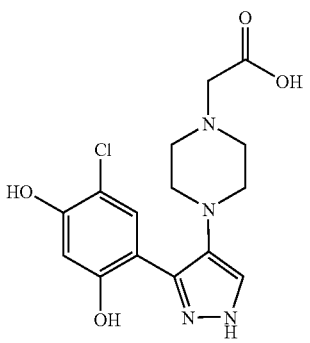 | 353 | A* |
| 47 | 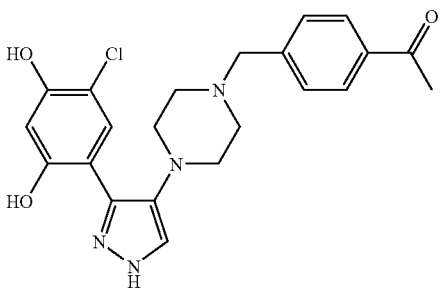 | 427 | A* |
| 48 | 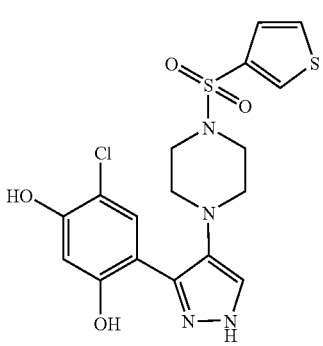 | 441 | A* |
tested in FP assay

EXAMPLE 49

4-Chloro-6-(5-methyl-4-piperazin-1-yl-1H-pyrazol-3-yl)-benzene-1,3-diol

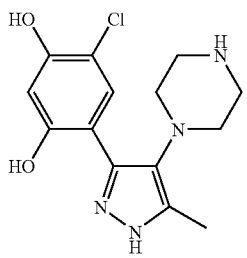

Step 1

4-[3-(2,4-Bis-benzyloxy-5-chloro-phenyl)-1-(toluene-4-sulfonyl)-1H-pyrazol-4-yl]-piperazine-1-carboxylic acid tert-butyl ester

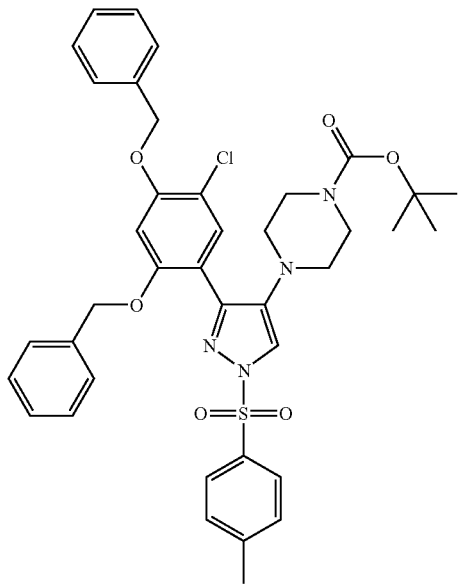

Para toluene sulphonyl chloride (180 mg, )0.95 mmol) was added to a stirred solution of 4-[3-(2,4-Bis-benzyloxy-5-chloro-phenyl)-1H-pyrazol-4-yl]-piperazine-1-carboxylic acid tert-butyl ester (500 mg, 0.9 mmol) in dichloromethane (10 ml) and pyridine (0.9 mmol). Stirring was continued for 18 h, then the solution was partitioned between water (20 ml) and ethyl acetate (2×20 ml). The combined organic phases were dried over magnesium sulphate, and concentrated in vacuo to leave a yellow oil. Purfication on silica (20 g) eluting with hexane, followed by hexane:diethyl ether, 1:1, then diethyl ether gave 4-[3-(2,4-Bis-benzyloxy-5-chloro-phenyl)-1-(toluene-4-sulfonyl)-1H-pyrazol-4-yl]-piperazine-1-carboxylic acid tert-butyl ester (490 mg, 77%)

LC retention time 3.22 minutes [M]+ 729.6 (Run time 3.75 mins)

Step 2

4-[3-(2,4-Bis-benzyloxy-5-chloro-phenyl)-5-methyl-1-(toluene-4-sulfonyl)-1H-pyrazol-4-yl]-piperazine-1-carboxylic acid tert-butyl ester

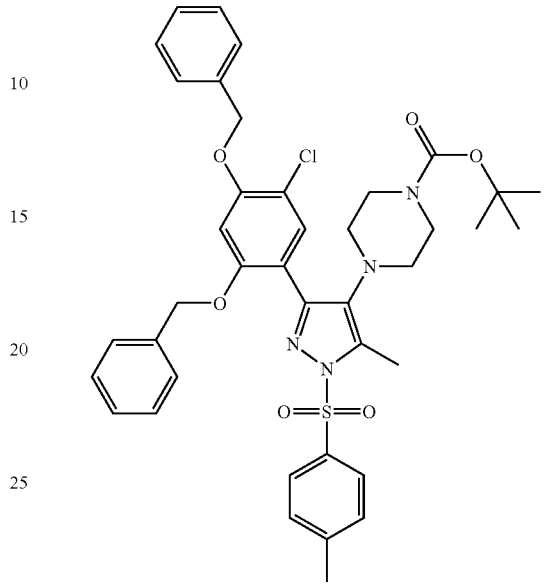

N-Butyl lithium (1.6M in hexane; 0.25 ml, 0.4 mmol) was added dropwise to a stirred, cooled (−78° C.) solution of 4-[3-(2,4-Bis-benzyloxy-5-chloro-phenyl)-1-(toluene-4-sulfonyl)-1H-pyrazol-4-yl]-piperazine-1-carboxylic acid tert-butyl ester) 240 mg, 0.33 mmol) in tetrahydrofuran (2 ml), under a nitrogen atmosphere. The mixture was stirred at −78° C. for 10 minutes, then methyl iodide (40 μL; 0.64 mmol) was added. The reaction mixture was warmed to room temperature, then partitioned between water (20 ml) and ethyl acetate (2×20 ml). The combined organic phases were dried over magnesium sulphate, then concentrated in vacuo, and purified on silica cartridge (200 mg) eluting with hexane, then hexane:diethyl ether, 1:1, then diethyl ether gave 4-[3-(2,4-Bis-benzyloxy-5-chloro-phenyl)-5-methyl-1-(toluene-4-sulfonyl)-1H-pyrazol-4-yl]-piperazine-1-carboxylic acid tert-butyl ester (70 mg; 29%)

LC retention time 3.26 minutes [M]+ 743.6 (Run time 3.75 mins)

The final product was obtained by the use of Method B of Example 1 and had activity 'A' in the Hsp90 FP assay.

EXAMPLE 50

4-Chloro-6-(5-hydroxymethyl-4-piperazin-1-yl-1H-pyrazol-3-yl)-benzene-1,3-diol

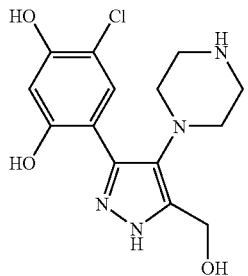

Step 1

4-[3-(2,4-Bis-benzyloxy-5-chloro-phenyl)-5-hydroxymethyl-1-(toluene4-sulfonyl)-1H-pyrazol-4-yl]-piperazine-1-carboxylic acid tert-butyl ester

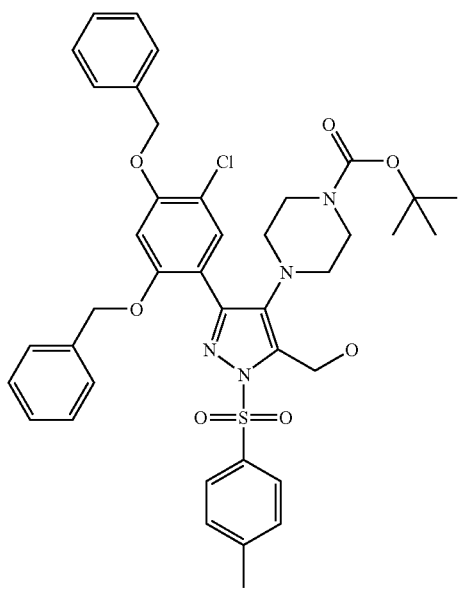

A solution of lithium aluminium hydride (1M in ether, 0.3 ml, 0.3 mmol) was added dropwise to a stirred solution of 4-[3-(2,4-Bis-benzyloxy-5-chloro-phenyl)-5-isobutoxycarbonyl-1-(toluene-4-sulfonyl)-1H-pyrazol-4-yl]-piperazine-1-carboxylic acid tert-butyl ester (90 mg, 0.11 mmol) [prepared by use of the lithiation chemistry in the preceding example] in anhydrous diethyl ether (2 ml) at room temperature, under a nitrogen atmosphere. The suspension was stirred 2 h then sodium hydroxide solution (1M, 3 drops) was added, followed by methanol (0.5 ml). The mixture was partitioned between water (30 ml) and ethyl acetate (2×20 ml), and the combined organic phases were dried over magnesium sulphate, then concentrated in vacuo to give 4-[3-(2,4-Bis-benzyloxy-5-chloro-phenyl)-5-hydroxymethyl-1-(toluene-4-sulfonyl)-1H-pyrazol-4-yl]-piperazine-1-carboxylic acid tert-butyl ester (58 mg, 88%)

LC retention time 2.87 minutes [M]+ 605.6 (Run time 3.75 mins)

Step 2

The final product was obtained by the use of Method B of Example 1.

The compound had activity 'A' in the Hsp90 FP assay.

EXAMPLE 51

5-(5-Chloro-2,4-dihydroxy-phenyl)-4-piperazin-1-yl-2H-pyrazole-3-carboxylic acid ethylamide

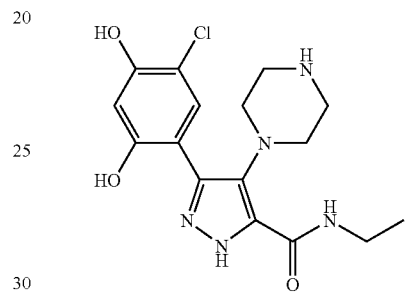

Prepared according to the lithiation chemistry in Examples 52 and 53, but quenching with ethyl isocyanate. The compound of this Example 54 had activity 'A' in the Hsp90 ATPase assay.

EXAMPLE 52

3-(4-Fluoro-2-hydroxyphenyl)-4-(piperazin-1-yl)-1H-pyrazole

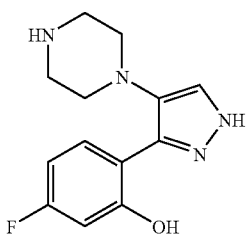

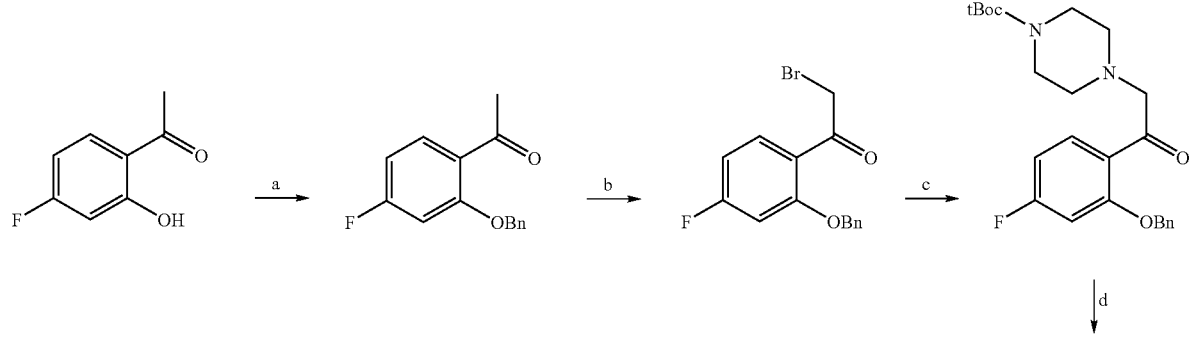

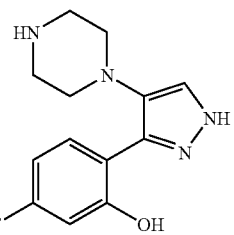 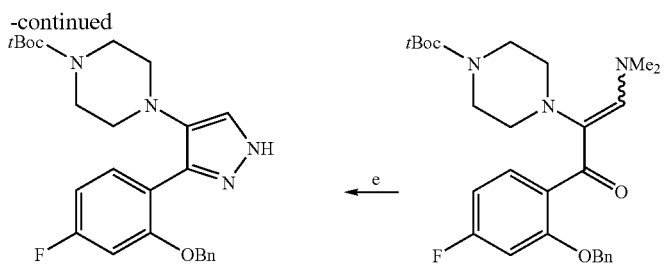

Reagents and Conditions: a. BnBr, K₂CO₃, DMF, rt, 18 h, 97%; b. PhNMe₃Br₃, THF, rt, 45 mins; c. ᵗBoc-piperazine, K₂CO₃, DMF, 80% (2 steps); d. DMFDMA, μ-wave 200° C., 15 min, e. NH₂NH₂·H₂O, EtOH, μ-wave, 120° C., 30 min, 33% (2 steps); f. BCl₃, DCM, 30%.

Step 1

2'-(Benzyloxy)-4'-fluoroacetophenone

Potassium carbonate (4.02 g, 29.10 mmol) was added to a solution of 4'-fluoro-2'-hydroxyacetophenone (2.0 mL, 2.56 g, 16.60 mmol) in DMF (15 mL). Benzyl bromide (2.07 mL, 2.98 g, 17.50 mmol) was added dropwise over 5 minutes at room temperature, and the mixture stirred for 18 h. The mixture was poured into hydrochloric acid (1.0 M in H₂O; 200 mL) and extracted with ethyl acetate (2×100 mL). The combined organic extracts were dried (MgSO₄) and the solvents removed in vacuo. Pure 2'-(benzyloxy)-4'-fluoroacetophenone (3.94 g, 97%) was obtained as a white powder after trituration with hexane. $R_f$ 0.44 (9:1 hexane:EtOAc); $\delta_H$ (CDCl₃) 7.82 (1H, dd, J=8.6 and 7.0 Hz), 7.43-7.38 (5H, m), 6.75-6.69 (2H, m), 5.13 (2H, s), 2.56 (3H, d, J=3.2 Hz); LCMS retention time 2.68 min, M+H⁺ 245.1.

Step 2

2'-(Benzyloxy)-2-bromo-4'-fluoroacetophenone

Phenyltrimethylammonium tribromide (1.55 g, 4.13 mmol) was added to a solution of 2'-(benzyloxy)-4'-fluoroacetophenone (1.01 g, 4.13 mmol) in THF (10 mL), and the mixture stirred at room temperature for 45 minutes, over which time the orange solution faded and a white precipitate formed. Tlc analysis (9:1 hexane:EtOAc) showed the reaction to be complete. The mixture was poured into water (20 mL) and extracted with ether (2×50 mL). The combined ethereal extracts were dried (MgSO₄) and the solvents removed in vacuo to give crude 2'-(benzyloxy)-2-bromo-4'-fluoroacetophenone as a colourless oil, which was used in the following step without purification. $R_f$ 0.47 (9:1 hexane:EtOAc); $\delta_H$ (CDCl₃) 7.89 (1H, dd, J=9.4 and 6.9 Hz), 7.45-7.40 (5H, m), 6.77-6.74 (2H, m), 5.15 (2H, s), 4.47 (2H, s); LCMS retention time 2.75 min, M+H⁺ 323.3/325.3.

Step 3

2'-(Benzyloxy)-2-[4-(tert-butoxycarbonyl)piperazin-1-yl]-4'-fluoroacetophenone 1-(tert-Butoxycarbonyl)piperazine (808 mg, 4.34 mmol) was added to a mixture of 2'-(benzyloxy)-2-bromo4'-fluoroacetophenone (assumed 4.13 mmol) and potassium carbonate (856 mg, 6.20 mmol) in DMF, and stirred for 18 h at room temperature. The solvent was removed in vacuo, the residue taken up in ethyl acetate (150 mL) and washed with water (100 mL) and brine (100 mL). The organice layer was dried (MgSO₄) and the solvents removed in vacuo. The crude product was purified by flash chromatography, eluting with 9:1 hexane:EtOAc followed by 1:1 hexane:EtOAc to give pure 2'-(benzyloxy)-2-[4-(tert-butoxycarbonyl)piperazin-1-yl]-4'-fluoroacetophenone (1.42 g, 80% over 2 steps) as a yellow oil; $R_f$ 0.00 (9:1 hexane:EtOAc), 0.50 (1:1 hexane:EtOAc); $\delta_H$ (CDCl₃) 7.89 (1H, dd, J=9.3 and 6.9 Hz), 7.48-7.44 (5H, m), 6.81-6.77 (2H, m), 5.17 (2H, s), 3.79 (2H, s), 3.51-3.47 (4H, m), 2.44-2.41 (4H, m), 1.50 (9H, s); LCMS retention time 2.10 min, M+H⁺ 429.4.

Step 4

3-[4-Fluoro-2-(benzyloxy)phenyl]-4-[4-(tert-butoxycarbonyl)piperazin-1-yl]-1H-pyrazole A solution of 2'-(benzyloxy)-2-[4-(tert-butoxycarbonyl)piperazin-1-yl]4'-fluoroacetophenone (270 mg, 0.63 mmol) in dimethylformamide dimethylacetal (1.5 mL) was heated in a sealed microwave tube at 200° C. for 15 minutes. A white precipitate formed. The mixture was evaporated to dryness in vacuo to give crude 4-[1-(2-benzyloxy-4-fluoro-benzoyl)-2-dimethylamino-vinyl]-piperazine-1-carboxylic acid tert-butyl ester. Ethanol (2 mL) and hydrazine hydrate (2.0 mL) were added and the mixture heated in a sealed microwave tube at 120° C. for 30 minutes. The crude mixture was loaded onto a dry pre-packed silica cartridge and dried overnight. The product was eluted with 2:1 hexane:EtOAc to give 4-[3-(2-benzyloxy-4-fluoro-phenyl)-1H-pyrazol-4-yl]-piperazine-1-carboxylic acid tert-butyl ester (95 mg, 33%) as a yellow gum; LCMS retention time 2.75 min, M+H⁺ 453.4.

Step 5

3-(4-Fluoro-2-hydroxyphenyl)-4-(piperazin-1-yl)-1H-pyrazole

Boron trichloride (1.0 M in DCM; 0.829 mL, 0.829 mmol) was added to a solution of 4-[3-(2-benzyloxy-4-fluoro-phenyl)-1H-pyrazol-4-yl]-piperazine-1-carboxylic acid tert-butyl ester (75 mg, 0.166 mmol) in DCM (7.5 mL). A brown precipitate formed. The mixture was stirred at room temperature for 1 hour and then poured into saturated aqueous sodium bicarbonate (50 mL) and extracted with DCM (3×50 mL). The combined organic layers were dried (MgSO₄) and the solvents removed in vacuo. The product was purified by preparative HPLC to give 3-(4-fluoro-2-hydroxyphenyl)4(piperazin-1-yl)-1H-pyrazole (13 mg, 30%) as an off-white solid; $\delta_H$ (MeOH-d₄) 7.96 (1H, br s), 7.72 (1H, s), 6.71-6.64 (2H, m), 3.36-3.33 (4H, m), 3.13-3.10 (4H, m), 2.65 (1H, s); LCMS retention time 1.46 min, M+H⁺ 263.2.

The compound of this Example 52 had activity 'B' in the Hsp90 ATPase assay.

EXAMPLE 53

3-[4-Acetamido-2-hydroxyphenyl]-4-(piperazin-1-yl)-1H-pyrazole

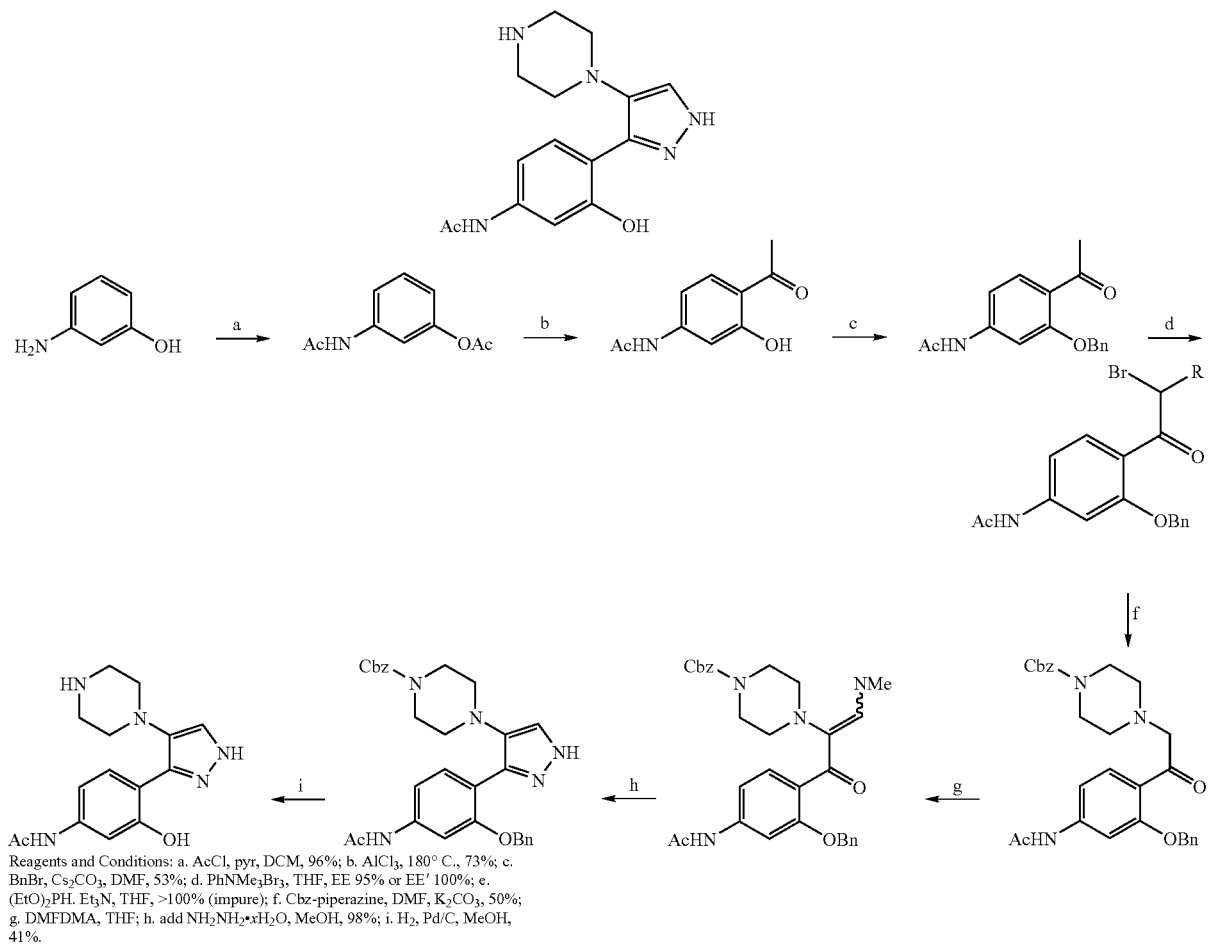

Reagents and Conditions: a. AcCl, pyr, DCM, 96%; b. AlCl₃, 180° C., 73%; c. BnBr, Cs₂CO₃, DMF, 53%; d. PhNMe₃Br₃, THF, EE 95% or EE' 100%; e. (EtO)₂PH. Et₃N, THF, >100% (impure); f. Cbz-piperazine, DMF, K₂CO₃, 50%; g. DMFDMA, THF; h. add NH₂NH₂·xH₂O, MeOH, 98%; i. H₂, Pd/C, MeOH, 41%.

Step 1

3-Acetamidophenyl acetate

Pyridine (46.32 mL, 45.30 g, 572 mmol) was added to a stirred suspension of 3-aminophenol (25.0 g, 229 mmol) in DCM (200 mL), and the mixture cooled to 0° C. A solution of acetyl chloride (14.45 mL, 15.95 g, 203.21 mmol) in DCM (100 mL) was added dropwise (CAUTION: Exotherm) to the mixture from a pressure-equalising dropping funnel over 2.5 hours, and the mixture stirred for a further 1 hour at 0° C. The mixture was poured into HCl (1.0 M in H₂O; 350 mL) and the layers separated. The aqueous layer was extracted with further DCM (150 mL), and the combined organic layers dried (MgSO₄) and the solvents removed in vacuo. The crude product was further dried for 18 h at 40° C., 150 mbar to give 3-acetamidophenyl acetate (42.5 g, 96%) as a white solid; $\delta_H$ (CDCl₃) 7.83 (1H, br s), 7.45 (1H, t, J=2.0 Hz), 7.23 (1H, t, J=8.1 Hz), 7.14-7.11 (1H, m), 6.78-6.76 (1H, m), 2.28 (3H, s), 2.06 (3H, s); LCMS retention time 1.76 min, M+H⁺ 194.2.

Step 2

4'-Acetamido-2'-hydroxyacetophenone

3-Acetamidophenyl acetate (10.47 g, 54.19 mmol) was ground to a fine powder in a pestle and mortar, then mixed with AlCl₃ (14.45 g, 108.40 mmol) in a 250 mL round-bottomed flask equiped with a bubbler attached to a nitrogen supply. The mixture was heated cautiously until melting (75° C.) and subsequent vigourous reaction (85° C.) had occurred (CAUTION: Vigourous exothermic reaction with evolution of gas. Note: The temperature at which these processes occurs shows some variation—the temperature indicated are the lowest observed, and the highest are approximately 30° C. higher for each process). The mixture was cooled to room temperature and the brown solid broken to a powder with a spatula. The mixture was then heated at 180° C. for 4.25 hours, and cooled to room temperature. The solid mass was broken up with a spatula, and ice-water (100 mL) was added. The mixture was stirred vigourously overnight and the pure product removed by filtration. The product was dried at reduced pressure (45° C., 100 mbar) for 18 hours to give N-(4-acetyl-3-hydroxy-phenyl)-acetamide (7.66 g, 73%) as an off-white powder; $\delta_H$ (DMSO-$d_6$) 12.32 (1H, s), 10.28 (1H, s), 7.83 (1H, d, J=8.8 Hz), 7.35 (1H, d, J=2.0 Hz), 7.05 (1H, dd, J=8.8, 2.0 Hz), 2.56 (3H, s), 2.07 (3H, s); LCMS retention time 1.87 min, M+H$^+$ 194.2.

Step 3

N-(4-Acetyl-3-benzyloxy-phenyl)-acetamide

Benzyl bromide (4.84 mL, 6.97 g, 40.76 mmol) was added dropwise over 5 minutes to a mixture of give N-(4-acetyl-3-hydroxy-phenyl)-acetamide (7.50 g, 38.82 mmol) and Cs$_2$CO$_3$ (25.30 g, 77.64 mmol) in DMF (175 mL) at room temperature. After stirring for 18 hours, the solvent was removed in vacuo, and the residue stirred vigourously with water (200 mL) and DCM (200 mL) until dissolution was complete. The layers were separated, and the aqueous further extractede with DCM (2×200 mL). The combined organic layers were dried (MgSO$_4$) and the solvents removed in vacuo. The residue was taken up in PhMe (150 mL) and evaporated to dryness, whereupon crystals started to form. The mixture was re-suspended in PhMe (100 mL) and refluxed for 1 hr with activated charcoal (5 g). The hot solution was filtered and allowed to cool. The product was collected by filtration to give N-(4-acetyl-3-benzyloxy-phenyl)-acetamide (5.79 g, 53%) as colourless crystals; $\delta_H$ (CDCl$_3$) 7.83 (1H, m), 7.76 (1H, d, J=8.5 Hz), 7.58 (1H, br s), 7.45-7.32 (6H, m), 6.74 (1H, dd, J=8.5, 1.9 Hz), 5.15 (2H, s), 2.56 (3H, s), 2.19 (3H, s); LCMS retention time 2.33 min, M+H$^+$ 284.3.

Step 4

N-[3-Benzyloxy-4-(2,2-dibromo-acetyl)-phenyl]-acetamide

Phenyltrimethylammonium tribromide (102 mg, 0.272 mmol) was added to a solution of N-(4-acetyl-3-benzyloxy-phenyl)-acetamide (35 mg, 0.124 mmol) in THF (3.5 mL), and stirred at room temperature for 2 hours. The mixture was partitioned between water (25 mL) and EtOAc (25 mL), the layers separated and the organic layer dried (MgSO$_4$). The solvents were removed in vacuo to give crude N-[3-benzyloxy-4-(2,2-dibromo-acetyl)-phenyl]-acetamide (54 mg, 100%) as a pale brown solid; $\delta_H$ (CDCl$_3$) 7.92 (1H, br s), 7.85 (1H, d, J=8.5 Hz), 7.55 (1H, br s), 7.50-7.35 (5H, m), 7.09 (1H, s), 6.78 (1H, dd, J=8.5, 1.9 Hz), 5.20 (2H, s), 2.21 (3H, s); LCMS retention time 2.65 min, M+H$^+$ 440.1/442.1/444.1. The mixture was used crude in the next step.

Step 5

N-[3-Benzyloxy-4-(2-bromo-acetyl)-phenyl]-acetamide

Method A
Phenyltrimethylammonium tribromide (241 mg, 0.641 mmol) was added to a stirred solution of N-(4-acetyl-3-benzyloxy-phenylacetamide (165 mg, 0.582 mmol) in THF (16 mL) and stirred at room temperature for 2 hours. The reaction mixture was poured into water (50 mL) and extracted with ether (2×50 mL). The combined ethereal extracts where dried (MgSO$_4$) and the solvents removed in vacuo to give crude N-[3-benzyloxy-4-(2-bromo-acetyl)-phenyl]-acetamide (200 mg, 95%) as an off-white solid; $\delta_H$ (CDCl$_3$) 7.98 (1H, br s), 7.92 (1H, br s), 7.81 (1H, d, J=8.5 Hz), 7.49-7.32 (5H, m), 6.82 (1H, dd, J=8.5, 1.9 Hz), 5.16 (2H, s), 4.50 (2H, s), 2.20 (3H, s); LCMS retention time 2.52 min, M+H$^+$ 362.2/364.2. The crude material was contaminated with a small amount of starting material and the corresponding dibromo-compound, but was sufficiently pure to use in step 6.

Method B
A solution of diethylphosphite (12.6 µL, 13.5 mg, 97.6 µmol) and triethylamine (13.6 µL, 9.9 mg, 97.6 µmol) in THF (0.1 mL) was added to a stirred solution of N-[3-benzyloxy-4-(2,2-dibromo-acetyl)-phenyl]-acetamide (41 mg, 92.9 µmol) in THF (1.5 mL) at room temperature, and the reaction stirred for 2 hours. The mixture was poured into EtOAc (20 mL) and washed with water (20 mL) and brine (20 mL). The organic layer was dried (MgSO$_4$) and the solvent removed in vacuo to give N-[3-benzyloxy-4-(2-bromo-acetyl)-phenyl]-acetamide (40 mg, >100%), which was seen by NMR to be contaminated with a diethylphosphite-derived contaminant. The material could be used successfully in the following steps without further purification. All analytical data was as reported above.

Step 6

4'-Acetamido-2'-benzyloxy-2-[4-(benzyloxycarbonyl)piperazin-1-yl]acetophenone 1-(Benzyloxycarbonyl)piperazine (117 µL, 134 mg, 0.607 mmol) was added to a mixture of N-[3-benzyloxy-4-(2-bromo-acetyl)phenyl]-acetamide (200 mg, 0.552 mmol) and potassium carbonate (115 mg, 0.828 mmol) in DMF (5 mL), and stirred at room temperature for 18 hours. The solvent was removed in vacuo, and taken up in brine (25 mL). The aqueous was extracted with DCM (3×25 mL) and the combined organics dried (MgSO$_4$). The solvents were removed in vacuo, and the product was purified by preparative HPLC to give pure 4'-acetamido-2'-benzyloxy-2-[4-(benzyloxycarbonyl)piperazin-1-yl]acetophenone (114 mg, 41%, 50% rec.) as an off-white solid; $\delta_H$ (CDCl$_3$) 8.23 (1H, br s), 7.81 (1H, d, J=8.6 Hz), 7.77-7.76 (1H, m), 7.53-7.51 (2H, m), 7.42-7.28 (8H, m), 7.08 (1H, dd, J=8.6, 1.8 Hz), 5.20 (2H, s), 5.12 (2H, s), 4.00 (2H, s), 3.59-3.48 (4H, m), 2.65-2.60 (4H, m), 2.14 (3H, s); LCMS retention time 2.07 min, M+H$^+$ 502.5, along with recovered N-(4-acetyl-3-benzyloxy-phenyl)-acetamide (35 mg).

Step 7

3-[4-Acetamido-2-benzyloxyphenyl]-4-[4-(benzyloxycarbonyl)-piperazin-1-yl]-1H-pyrazole A solution of 4'-acetamido-2'-benzyloxy-2-[4-(benzyloxycarbonyl)piperazin-1-yl]acetophenone (68 mg, 135.6 µmol) and dimethylformamide dimethylacetal (90 µL, 81 mg, 677.9 µmol) in dry THF (0.5 mL) was sealed in a microwave tube and heated at 120° C. for 65 minutes. Further dimethylformamide dimethylacetal (90 µL, 81 mg, 677.9 µmol) in THF (0.5 mL) was added and the tube heated again for 40 minutes at 120° C.

To the resulting solution of crude 4-[1-(acetylamino-2-benzyloxy-benzoyl)-2-dimethylamino-vinyl]-piperazine-1-carboxylic acid benzyl ester was added hydrazine hydrate (0.75 mL) and MeOH (0.75 mL) in order to make the mixture monophasic, and the mixture stirred at room temperature for 3 days. The volatiles were removed in vacuo, and the residue poured into 50% saturated brine (100 mL). The product was extracted with EtOAc (3×100 mL), the combined organics dried (MgSO$_4$) and the solvents removed in vacuo to give crude 3-[4-acetamido-2-benzyloxyphenyl]-4-[4-(benzyloxycarbonyl)piperazin-1-yl]-1H-pyrazole (70 mg, 98%) as a yellow gum; LCMS retention time 2.48 min, M+H$^+$ 526.5.

Step 8

3-[4-Acetamido-2-hydroxyphenyl]-4-(piperazin-1-yl)-1H-pyrazole

A solution of 3-[4-acetamido-2-benzyloxyphenyl]-4-[4-(benzyloxycarbonyl)piperazin-1-yl]-1H-pyrazole (70 mg, 133.2 μmol) in MeOH (7 mL) was degassed (3× vacuum/nitrogen) and palladium (10% on carbon; 10 mg, cat.) added. The reaction mixture was again degassed (3× vacuum/nitrogen) and the atmosphere replaced with one of hydrogen (3× vacuum/hydrogen). The mixture was shaken at room temperature for 18 hours. The catalyst was removed by filtration through a small pad of celite and washed with further MeOH (15 mL). The solvent was removed in vacuo to give crude product, which was purified by preparative HPLC to give 3-[4-acetamido-2-hydroxyphenyl]-4-(piperazin-1-yl)-1H-pyrazole (16.3 mg, 41%) as a white solid; $\delta_H$(MeOH-$d_4$) 8.47 (1H, s), 7.80 (1H, br s), 7.68 (1H, s), 7.26 (1H, s), 7.11 (1H, dd, J=8.5, 2.1 Hz), 3.34-3.29 (4H, m), 3.11-3.07 (4H, m), 2.12 (3H, s); LCMS retention time 1.26 min, M+H$^+$ 302.3.

The compound of this Example 53 had activity 'B' in the Hsp90 FP binding assay.

EXAMPLE 54

3-Methyl-5-(4-piperazin-1-yl-1H-pyrazol-3-yl)-1H-indol-6-ol

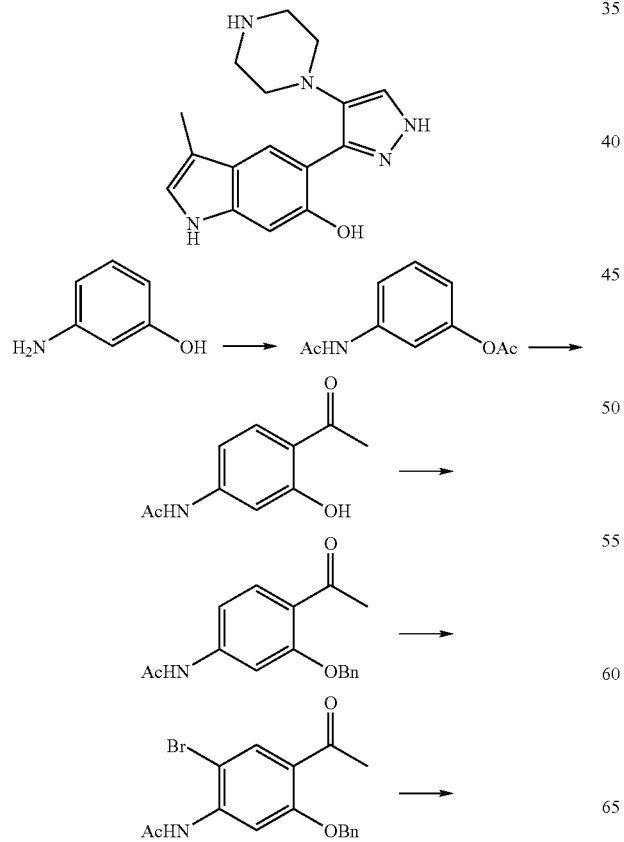

-continued

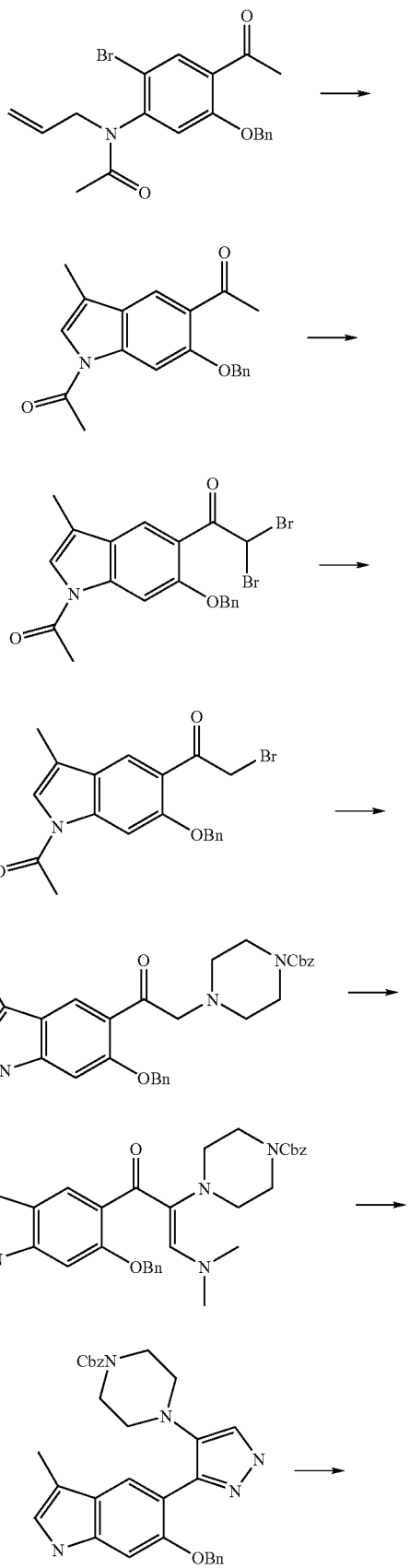

-continued

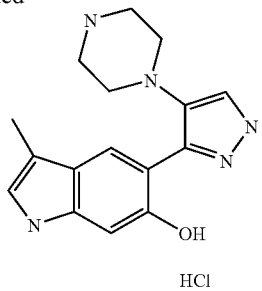

HCl

Step 1

N-(4-Acetyl-3-hydroxy-phenyl)-acetamide

Acetic acid 3-acetylamino-phenyl ester (5.0 g, 25.9 mmol) was ground to a fine powder and then combined with AlCl$_3$ (6.9 g, 52.3 mmol) in a round bottomed flask. After flushing with nitrogen, the flask was heated to 95° C. and held at this temperature until the reaction had finished fuming. The reaction was allowed to cool to room temperature and the brown solid crushed to a powder. The reaction was then reheated to 180° C. After 4 hours, the reaction was cooled to room temperature and crushed to form a powder. Ice water (100 ml) was added and the reaction stirred overnight. The product was filtered, washed with water and dried to afford a brown solid (2.57 g, 51.4%). LC/MS: RT=1.864 min. 194 (MH$^+$).

Step 2

N-(4-Acetyl-3-benzyloxy-phenyl)-acetamide

N-(4-Acetyl-3-hydroxy-phenyl)acetamide (2.57 g, 13.3 mmol) was suspended in DMF (60 ml), followed by the sequential addition of Cs$_2$CO$_3$ (8.70 g, 26.7 mmol) and benzyl bormide (1.7 ml, 14 mmol). The reaction was stirred at room temperature overnight. The solvent was removed in vacuo and the oily residue stirred in DCM/H$_2$O (1:1). The organics were washed with water, dried (Na$_2$SO$_4$) and purified by column chromatography in a gradient of hexane to 1:1 hexane/EtOAc to afford the benzyl ether as a cream solid (1.25 g, 33%). LC/MS: RT=2.307 min. 284 (MH$^+$).

Step 3

N-(4-Acetyl-5-benzyloxy-2-bromo-phenyl)-acetamide

N-Bromosuccinimide (0.756 g, 4.27 mmol) was added portionwise to a solution of N-(4-acetyl-3-benzyloxy-phenyl)-acetamide (1.2 g, 4.24 mmol) in DMF (24 ml) and the reaction stirred overnight at room temperature. The reaction mixture was diluted with DCM, washed with water and dried over MgSO$_4$ to afford a white solid (1.03 g, 67%). LC/MS: RT=2.609 min. 362/364 (MH$^+$).

Step 4

N-(4-Acetyl-5-benzyloxy-2-bromo-phenyl)-N-allyl-acetamide

A solution of N-(4-acetyl-5-benzyloxy-2-bromo-phenyl)-acetamide (1.03 g, 2.85 mmol) in anhydrous THF (20 ml) under nitrogen was cooled to −78° C. followed by the dropwise addition of LDA (2.1 ml, 2M solution, 4.3 mmol). The reaction was continued to stir for an hour at −78° C. and then quenched with allyl bromide (0.44 ml, 2.85 mmol). The reaction was allowed to warm to room temperature and continued to stir overnight. The solution was partitioned between EtOAc and water. The organics were collected and washed with water, brine and then dried (MgSO$_4$). Purification by column chromatography in hexane/EtOAc (1:1) afforded a white solid (0.662 g, 58%). LC/MS: RT=2.703 min. 402/404 (MH$^+$).

Step 5

1-(1-Acetyl-6-benzyloxy-3-methyl-1H-indol-5-yl)-ethanone

A solution of N-(4-acetyl-5-benzyloxy-2-bromo-phenyl)-N-allyl-acetamide (0.662 g, 1.65 mmol), P(o-tolyl)$_3$ (0.028 g, 0.092 mmol) and triethylamine (0.34 ml, 2.24 mmol) in MeCN (15 ml) was flushed with nitrogen, followed by the addition of a Pd(OAc)$_2$ (0.005 g). The reaction was microwaved for 500 sec. at 150° C. The crude mixture was diluted with EtOAc, washed with water and dried over MgSO$_4$. Purification by column chromatography in hexane/EtOAc (1:1) afforded (0.283 g, 54%) a cream solid. LC/MS: RT=2.742 min. 322 (MH$^+$), 344 (MNa$^+$), 280 (MH$^+$-Ac).

Step 6

1-(1-Acetyl-6-benzyloxy-3-methyl-1H-indol-5-yl)-2,2-dibromo-ethanone

To a solution of 1-(1-acetyl6-benzyloxy-3-methyl-1H-indol-5-yl)-ethanone (0.283 g, 0.88 mmol) in anhydrous THF (6 ml) was added PhNMe$_3$Br$_3$ (0.497 g, 2.3 mmol). The reaction was stirred for 1 hour at room temperature. The solution was diluted with water and the organics extracted with Et$_2$O and dried over MgSO$_4$ to afford the crude product (0.420 g, >90%). LC/MS: RT=2.900 min. 478/480 (MH$^+$).

Step 7

1-(1-Acetyl-6-benzyloxy-3-methyl-1H-indol-5-yl)-2-bromo-ethanone

The crude product 1-(1-acetyl-6-benzyloxy-3-methyl-1H-indol-5-yl)-2,2-dibromo-ethanone (0.42 g, 0.88 mmol) was suspended in THF (4 ml), followed by the addition of triethylamine (0.12 ml, 0.89 mmol) and (EtO)$_2$P(O)H (0.137 ml, 0.88 mmol). After stirring overnight at room temperature, the reaction was diluted with EtOAc, washed with H$_2$O, brine and dried over MgSO$_4$. The solvent was removed in vacuo and the crude product purified by column chromatography in hexane/EtOAc (1:1) to give the product (0.039 g, 11%). LC/MS: RT=2.830 min. 400/402 (MH$^+$).

Step 8

4-[2-(6-Benzyloxy-3-methyl-1H-indol-5-yl)-2-oxo-ethyl]-piperazine-1-carboxylic acid benzyl ester Compound 1-(1-acetyl-6-benzyloxy-3-methyl-1H-indol-5-yl)-2-bromo-ethanone (0.039 g, 0.1 mmol), K$_2$CO$_3$ (0.019 g, 0.14 mmol) and Cbz-piperidine (0.026 ml, 0.1 mmol) was stirred in DMF (2 ml) at room temperature for 5 hours. The solvent was removed in vacuo and the residue redissolved in DCM and washed with water, brine, dried over MgSO$_4$. Purification by column chromatography in hexane/EtOAc (3:2) afforded the product (0.008 g, 17%). LC/MS: RT=2.236 min. 498 (MH$^+$).

Step 9

4-[1-(6-Benzyloxy-3-methyl-1H-indole-5-carbonyl)-2-dimethylamino-vinyl]-piperazine-1-carboxylic acid benzyl ester A solution of 4-[2-(6-benzyloxy-3-methyl-1H-indol-5-yl)-2-oxo-ethyl]-piperazine-1-carboxylic acid benzyl ester (0.661 g, 1.33 mmol) in DMFDMA (5 ml) was heated at 100° C. overnight. The solvent was removed in vacuo and the crude product purified by column chromatography in hexane/EtOAc (1:1) to afford the product (0.158 g, 22%). LC/MS: RT=5.33 min. 553 (MH$^+$).

Step 10

4-[3-(6-Benzyloxy-3-methyl-1H-indol-5-yl)-1H-pyrazol-4-yl]-piperazine-1-carboxylic acid benzyl ester A solution of 4-[1-(6-benzyloxy-3-methyl-1H-indole-5-carbonyl)-2-dimethylamino-vinyl]-piperazine-1-carboxylic acid benzyl ester (0.158 g, 0.29 mmol) and hydrazine (0.75 ml, 15.5 mmol) in EtOH was refluxed for 1 hour, after which time the reaction had gone to completion. The solvent was removed in vacuo and the product purified by column chromatography in hexane/EtOAc (1:1) to afford an off-white solid (0.0445 g, 30%). LC/MS: RT=2.713 min. 522 (MH$^+$).

Step 11

3-Methyl-5-(4-piperazin-1-yl-1H-pyrazol-3-yl)-1H-indol-6-ol

A solution of 4-[3-6-benzyloxy-3-methyl-1H-indol-5-yl)-1H-pyrazol-4-yl]-piperazine-1-carboxylic acid benzyl ester (0.022 g, 0.042 mmol) in MeOH (2 ml) was evacuated and flushed with nitrogen. 10% Pd/C (10 mg) was added to the solution and the suspension was evacuated and flushed with hydrogen. The reaction was shaken at room temperature under a hydrogen atmosphere overnight. The reaction was filtered through celite and the solvent removed in vacuo. The final product was salted with HCl/Et$_2$O and triturated with ether to afford a pale brown solid (0.0046 g, 33%). LC/MS: 1.495 min. 298 (MH$^+$).

The compound of this Example 54 had activity 'B' in the Hsp90 FP binding assay.

The compounds of Examples 55-64 below, containing a resorcinol ring substituted with bromine, were prepared analogously to Scheme 1 but via the bromo analogue of the intermediate of Step 3 of Example 1. That bromo intermediate was prepared according to Scheme 6 as follows:

Scheme 6

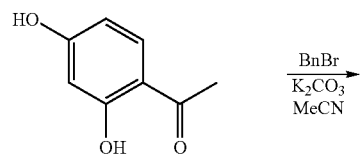

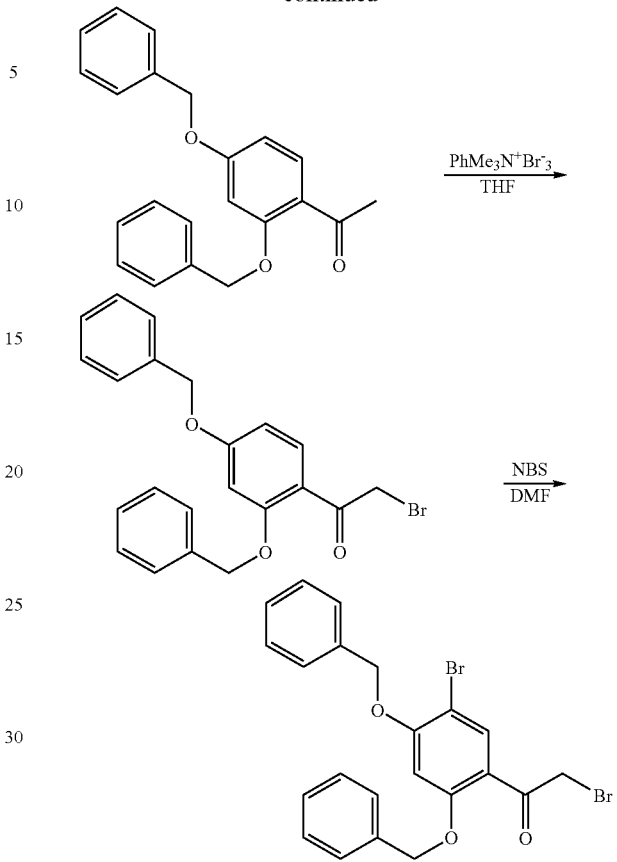

Step 1

1-(2,4-Bis-benzyloxyphenyl)-ethanone

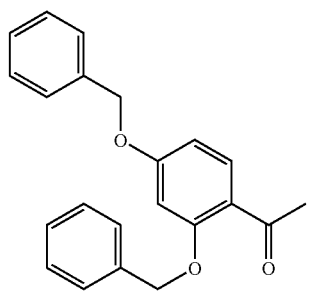

Benzyl bromide (35.6 mL, 0.3 mol) was added to a suspension of 2,4-dihydroxyacetophenone (15 g, 0.1 mol) and potassium carbonate (41.4 g, 0.3 mol) in acetonitrile (150 mL) and the mixture stirred overnight. After concentration to dryness, the residues were resuspended in dichloromethane (100 mL) and washed with water (100 mL). The organic phase was dried over magnesium sulphate and concentrated. Trituration with hexanes, filtration and drying in vacuo gave 1-(2,4-Bis-benzyloxyphenyl)-ethanone as a white powder (26 g).

LC retention time 2.83 minutes, [M+H]$^+$ 333.3 (Run time 3.75 min)

Step 2

1-(2,4-Bis-benzyloxyphenyl)-2-bromo-ethanone

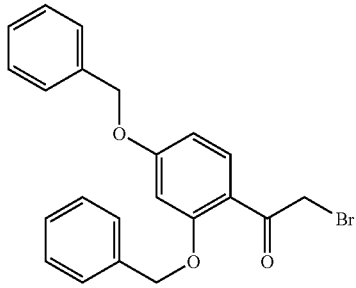

Phenyltrimethylammonium tribromide (5.6 g, 0.015 mol) was added portionwise to a stirred solution of 1-(2,4-Bis-benzyloxyphenyl)-ethanone (5.0 g, 0.015 mol) in tetrahydrofuran (50 ml) and the mixture was stirred for 2 h. The mixture was partitioned between water (50 ml) and diethyl ether (2×50 ml). The combined organic phases were dried over magnesium sulphate and concentrated to give 1-(2,4-Bis-benzyloxyphenyl)-2-bromo-ethanone as a beige solid which was used without further purification.

LC retention time 2.89 minutes, [M+H]$^+$ 411.2 and 413.2 (Run time 3.75 min)

Step 3

1-(2,4-Bis-benzyloxy-5-bromo-phenyl)-2-bromo-ethanone

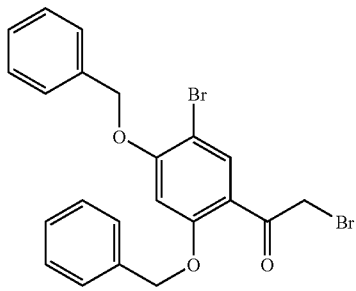

N-bromo succinimide (2.67 g, 0.015 mol) was added to a stirred solution of crude 1-(2,4-Bis-benzyloxyphenyl)-2-bromo-ethanone (ca. 6.16 g, 0.015 mol) in dimethylformamide (50 ml) and the mixture was stirred for 18 h. The mixture was concentrated to dryness, dissolved in dichloromethane (50 mL) and washed with (2×50 ml). The combined organic phases were dried over magnesium sulphate and concentrated to give 1-(2,4-Bis-benzyloxy-5-bromo-phenyl)-2-bromo-ethanone as a white solid, which was used without further purification.

LC retention time 2.99 minutes, [M+Na]$^+$ 511.2, 513.2 and 515.2 (Run time 3.75 min)

In the following table of Examples, the entries in the column "Hsp90 IC50" are again the results obtained in the ATPase assay described below:

| Example | Structure | MH+ | Hsp90 IC50 |
|---|---|---|---|
| 55 | 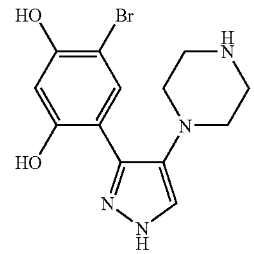 | 339, 341 | B |
| 56 | 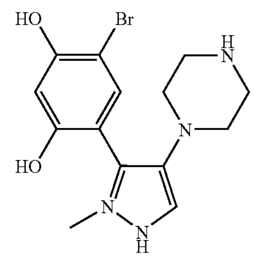 | 353, 355 | B |
| 57 | 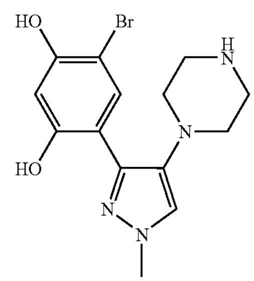 | 353, 355 | B |
| 58 | 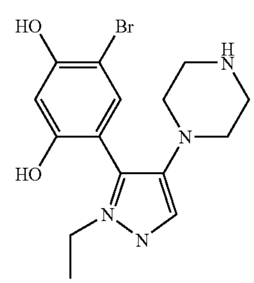 | 367, 369 | B |

| Example | Structure | MH+ | Hsp90 IC50 |
|---|---|---|---|
| 59 | (structure) | 367, 369 | B |
| 60 | (structure) | 381, 383 | B |
| 61 | (structure) | 381, 383 | B |
| 62 | (structure) | 429, 431 | B |
| 63 | (structure) | 429, 431 | B |
| 64 | (structure) | 425, 427 | B |

The compounds of Examples 65-76 below were prepared using the compound of Example 55 as an intermediate. For example, the compound of Example 70 was prepared as follows, and the compounds of the additional Examples 65-69 and 71-76 were prepared analogously.

Step 1

Coupling of Bromo Intermediate to Form Styryl Intermediate

A mixture of 4-bromo-6-(4-piperazin-1-yl-1H-pyrazol-3-yl)-benzene-1,3-diol (Example 58) (1 equiv.), 4-fluorostyrene (3 equiv.) and N,N-diisopropylethylamine (3 equiv.) in n-butanol (50 mL per equiv.) was degassed (3× nitrogen/vacuum). Dichlorobis(tri-o-tolylphosphino)palladium(II) (2 mol %) was added and the mixture heated under reflux for 15 hours. The mixture was filtered through a small plug of silica and the silica washed with dichloromethane.

Step 2

Reduction to Phenethyl Compounds

A solution of sodium acetate (1.0 M in H₂O, 3 equiv.) was added dropwise over 2 hours to a refluxing solution of alkene (1 equiv.) and p-toluenesulphonyl hydrazide (3 equiv.) in 1,2-DME, and refluxing continued for 20 hours. The mixture was cooled, poured into water and extracted with dichloromethane. The combined extracts were dried (MgSO₄) and concentrated in vacuo. The crude product was purified by flash chromatography.

| Example | Structure | MH+ | Hsp90 IC50 |
|---|---|---|---|
| 65 | 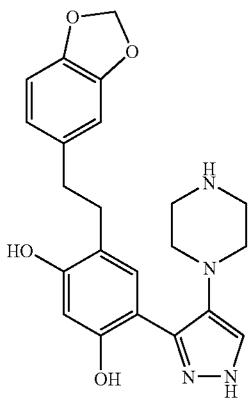 | 409 | A |
| 66 | 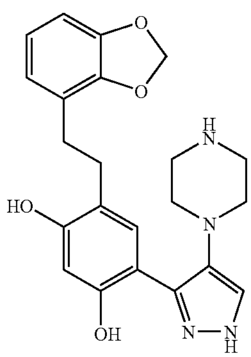 | 409 | A |
| 67 | 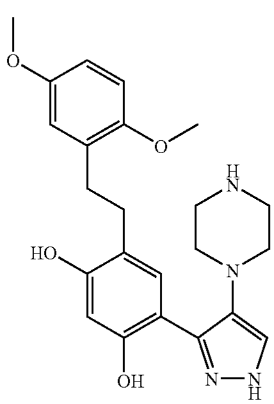 | 425 | A |
| 68 | 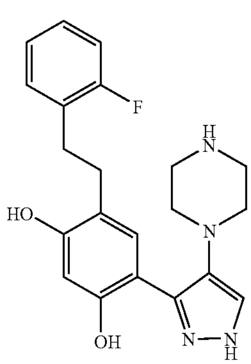 | 383 | A |
| 69 | | 383 | A |
| 70 | | 383 | A |
| 71 | | 379 | A |
| 72 | | 379 | A |

61

-continued

| Example | Structure | MH+ | Hsp90 IC50 |
|---|---|---|---|
| 73 | 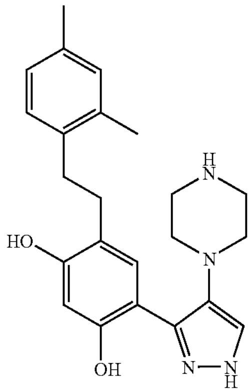 | 393 | A |
| 74 | 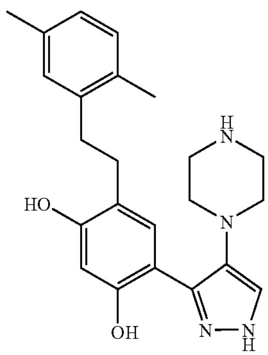 | 393 | A |
| 75 | 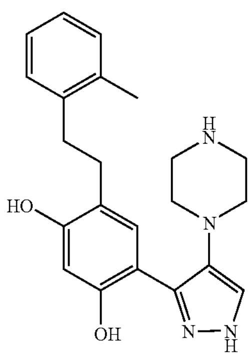 | 379 | A |
| 76 | 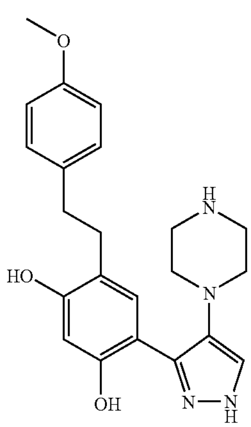 | 395 | A |

62

EXAMPLE 77

4-Bromo-6-{4-[4-(4-methanesulfonyl-benzylamino)-piperidin-1-yl]-1H-pyrazol-3-yl}-benzene-1,3-diol

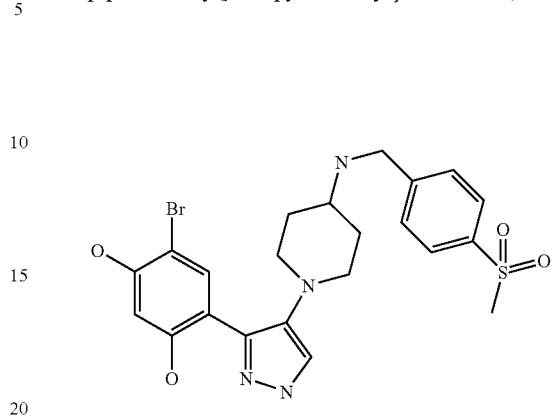

Step 1

8-[3-(2,4-Bis-benyloxy-5-bromo-phenyl)-1H-pyrazol-4-yl]-1,4-dioxa-8-aza-spiro[4.5]decane

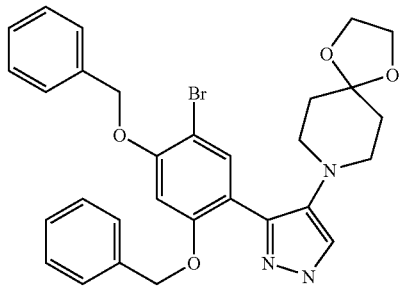

1-(2,4-Bis-benzyloxy-5-bromo-phenyl)-2-bromo-ethanone (prepared according to Scheme 6 above) (15.56 g, 31.74 mmol) was dissolved in dimethylformamide (20 ml). 1,4-Dioxa-8-aza-spiro[4.5]decane (4.55 g, 31.74 mmol) and triethylamine (4.42 ml, 31.74 mmol) were added and the reaction was stirred at room temperature for 1 hour. The solvent was removed under reduced pressure. The residue was taken up in dimethylformamide dimethylacetal (60 ml, 452 mmol) and stirred at 110° C. for 16 hours. The reaction was cooled to room temperature and concentrated in vacuo to leave a brown oil. This was dissolved in ethanol (100 ml) and hydrazine hydrate (23.8 g, 476 mmol) and refluxed for 16 hours. The reaction was cooled to room temperature and evaporated to dryness and purified on silica gel by flash chromatography. The product was eluted with ethyl acetate/hexane (1:1), the combined fractions were evaporated and the residue was triturated with diethyl ether to yield an off-white solid (6.31 g).

LC retention time 2.79 minutes [M+H]+ 576.4 and 578.4 (bromine splitting pattern) (Run time 3.75 min)

Step 2

1-[3-(5-Bromo-2,4-dihydroxy-phenyl)-1H-pyrazol-4-yl]-piperidin-4-one

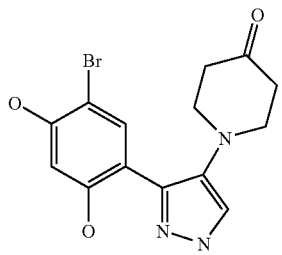

8-[3-(2,4-Bis-benyloxy-5-bromo-phenyl)-1H-pyrazol-yl]-1,4-dioxa-8-aza-spiro[4.5]decane (6.55 g, 11.4 mmol) was dissolved in dichloromethane (70 ml) and cooled to 0° C. Boron trichloride (1 M in dichloromethane, 57 ml, 57 mmol) was added dropwise. The reaction was warmed to room temperature and stirred for 30 minutes. It was then quenched with water (50 ml) at 0° C., warmed to room temperature and stirred for 3 days. The reaction was neutralised to pH=7 with saturated aqueous sodium hydrogencarbonate solution, the light brown precipitate was filtered off and washed with water and then dried in a vacuum oven (2.25 g).

LC retention time 1.89 minutes [M+H]$^+$ 352.4 and 354.2 (bromine splitting pattern) (Run time 3.75 min)

Step 3

4Bromo-6-{4-[4-(4-methanesulfonyl-benzylamino)-piperidin-1-yl]-1H-pyrazol-3-yl}-benzene-1,3-diol

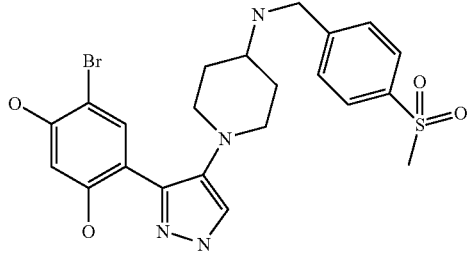

1-[3-(5-Bromo-2,4-dihydroxy-phenyl)-1H-pyrazol-4yl]-piperidin-4-one (0.1 g, 0.284 mmol) was dissolved in methanol (3 ml). Triethylamine (0.044 ml, 0.312 mmol) and 4-methanesulfonyl-benzylamine hydrochloride (0.069 g, 0.312 mmol) were added and the reaction was stirred at room temperature for 1 hour. Excess sodium borohydride was added and the solvent was removed in vacuo when the fizzing ceased. The residue was purified on silica by flash chromatography. The product eluted in methanol/dichloromethane (1:9). Further purification by HPLC was necessary. White solid, yield 0.036 g.

LC retention time 1.68 minutes [M+H]$^+$ 521.3 and 523.3 (bromine splitting pattern) (Run time 3.75 min)

The compounds of Examples 78-88 were prepared analogously to the compound of Example 80 by reaction in Step 5 of appropriate amine with the Step 4 intermediate. Again the entries in the column "Hsp90 IC50" are the results obtained in the ATPase assay described below:

| Example | Structure | MH+ | Hsp90 IC50 |
|---|---|---|---|
| 78 | 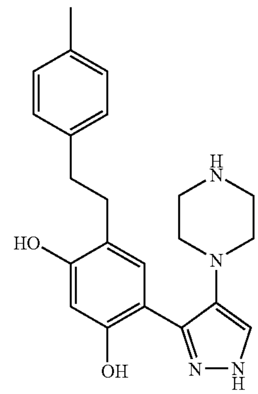 | 355, 357 | B |
| 79 | 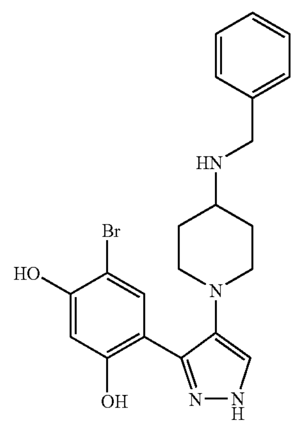 | 444, 446 | A |
| 80 | 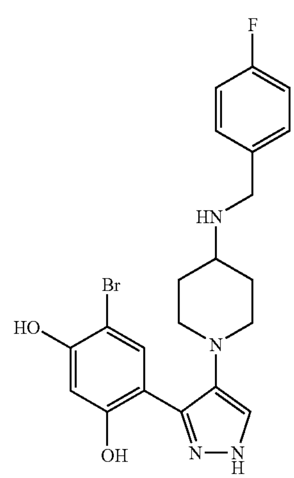 | 462, 464 | A |

| Example | Structure | MH+ | Hsp90 IC50 |
|---|---|---|---|
| 81 | 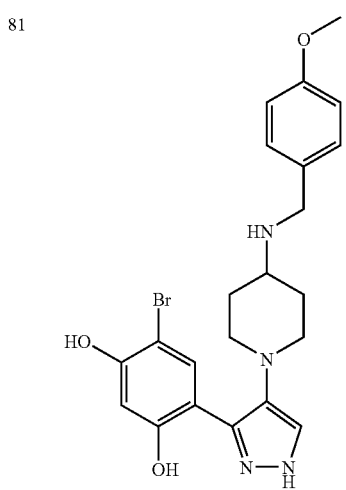 | 474, 476 | A |
| 82 | 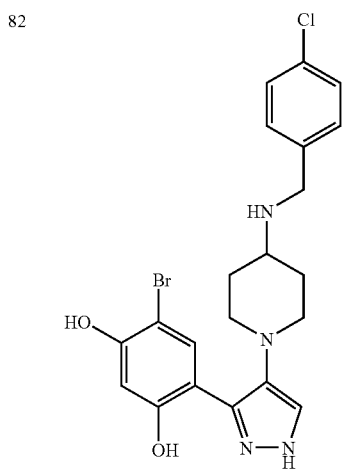 | 478, 480 | A |
| 83 | 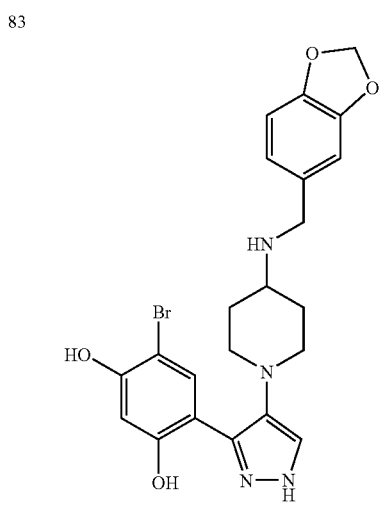 | 488, 490 | A |
| Example | Structure | MH+ | Hsp90 IC50 |
|---|---|---|---|
| 84 | 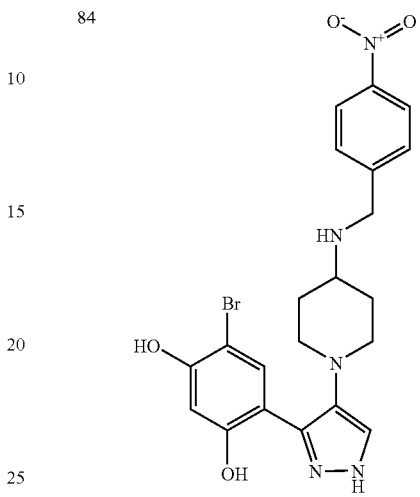 | 489, 491 | A |
| 85 | 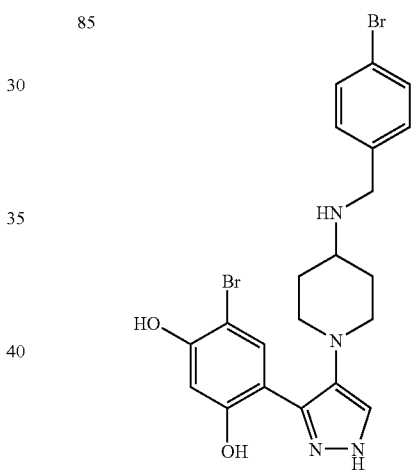 | 523, 525 | A |
| 86 | 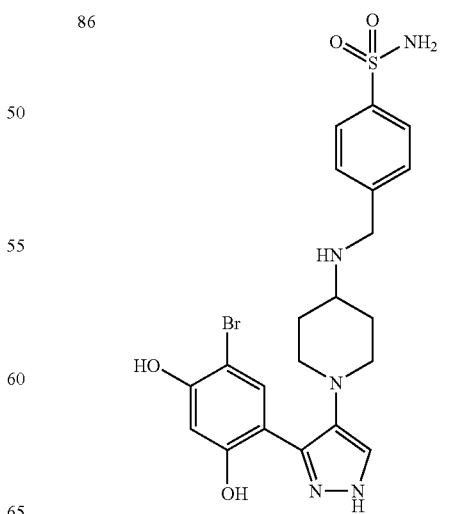 | 523, 525 | A |

-continued

| Example | Structure | MH+ | Hsp90 IC50 |
|---|---|---|---|
| 97 | (structure) | 382, 384 | A |
| 98 | (structure) | 399, 401 | A |

Biological Results

The intrinsic ATPase activity of HSP90 may be measured using yeast HSP90 as a model system. The assay, based on the use of malachite green for the measurement of inorganic phosphate, was used to test the HSP90 inhibitory activity of the compounds of the Examples herein.

Malachite Green ATPase Assay

Materials

Chemicals are of the highest purity commercially available and all aqueous solutions are made up in AR water. Because of the need to minimise contamination with inorganic phosphate, precautions should be taken with solutions and apparatus used in the assays. Glassware and pH meters are rinsed with double distilled or deionised water before use and, wherever possible, plastic ware should be used. Gloves are worn for all procedures.

(1) Greiner 384-well (Greiner 781101) or Costar 384-well flat-bottomed polystyrene multiwell plates (VWR).
(2) Assay buffer of (a) 100 mM Tris-HCl, pH 7.4, (b) 150 mM KCl, (c) 6 mM $MgCl_2$. Stored at room temperature.
(3) 0.0812% (w/v) malachite green (M 9636, Sigma Aldrich Ltd., Poole, UK). Stored at room temperature.
(4) 2.32% (w/v) polyvinyl alcohol USP (P 1097, Sigma Aldrich Ltd, Poole, UK) in boiling water (see Comment 1), allowed to cool, and stored at room temperature.
(5) 5.72% (w/v) ammonium molybdate in 6 M hydrochloric acid. Stored at room temperature.
(6) 34% (w/v) sodium citrate. Stored at room temperature.
(7) 100 mM ATP, disodium salt, special quality (47699, Sigma Aldrich). Stored at −20° C.
(8) *E. coli* expressed yeast HSP90 protein, purified >95% (see, e.g., Panaretou et al., 1998) and stored in 50 uL aliquots at −80° C.

Method

1. Dilute test compounds to 500 µM in AR water (DMSO concentration will be 2.5%). Transfer 2.5 µl of these compounds directly from the daughter plate to the assay plate, giving a final assay concentration of 100 µM. To obtain 12 point IC50 values, perform serial dilutions 1:2 to produce a range of assay concentrations from 100 µM to 97.6 nM (2.5% DMSO), and transfer 2.5 µl of each concentration into the assay plate. Column 1 in the assay plate contains no compound, as a negative control. An additional row with no compound is also used as a background.
2. Prepare ATP by diluting 100 mM stock to 925 µM with assay buffer, and aliquot 5 µl of diluted ATP to each well including controls (final assay concentration 370 µM).
3. Add 5 µl of buffer to background row.
4. Dilute enzyme preparation to 1.05 µM with assay buffer, and aliquot 5 µl into each compound well and to the negative control column.
5. Collect the reagents to the bottom of the well, cover plate with plate seal and incubate overnight at 37 degC.
6. First thing in the morning prepare the Malachite Green Reagent. Add 2 parts of Malachite Green Solution, 1 part of Polyvinyl Alcohol Solution, 1 part of Ammonium Molybdate Solution, and 2 parts of AR water.
7. Invert to mix, and leave for approximately 1 hour until the colour turns from brown to golden yellow.
8. Add 40 µl of Malachite Green Reagent to each well, allow 5 mins for colour to develop.
9. Add 5 µl of Sodium Citrate Reagent to each well (see comment 2)
10. Re-cover with plate seal and shake on plate shaker for at least 15 mins.
11. Measure Absorbance at 620 nM using a suitable plate reader (e.g. Victor, Perkin Elmer Life Sciences, Milton Keynes, UK). Under these conditions, the control absorbance is 0.9 to 1.4, and the background is 0.2-0.35 giving a signal to noise ratio of ~12. The Z' factor calculated from data obtained using these conditions is between 0.6 and 0.9.

Comments (1) The polyvinyl alcohol dissolves in boiling water with difficulty and stirring for 2-3 h is required.
(2) The time interval between addition of the malachite green reagent and the sodium citrate should be kept as short as possible in order to reduce the non-enzymatic hydrolysis of ATP. Once the sodium citrate is added, the colour is stable for up to 4 h at room temperature.
(3) Compounds can be added to the assay plates using a Biomek FX Robot (Beckman Coulter). A Multidrop 384 dispenser (Thermo Labsystems, Basingstoke, UK) can be conveniently used to add reagents to the plate.
(4) The assay conditions were optimised with respect to time, protein and substrate concentration in order to achieve minimal protein concentration whilst retaining signal to noise differential.
(5) Signal to noise (S/N) is calculated using the following equation:

$$(S-B)/\sqrt{(SD \text{ of } S)^2 + (SD \text{ of } B)^2}$$

(6) To determine specific activity of HSP90, a range of inorganic phosphate concentrations (0-10 µM) are prepared and the absorbance at 620 nm measured as described. Specific activity is calculated from the resulting calibration curve.

The compounds tested in the above assay were assigned to one of two activity ranges, namely A=<50 μM; B=>50 μM, and those assignments are reported above.

Fluorescence Polarization Assay

Fluorescence polarization {also known as fluorescence anisotropy} measures the rotation of a fluorescing species in solution, where the larger molecule the more polarized the fluorescence emission. When the fluorophore is excited with polarized light, the emitted light is also polarized. The molecular size is proportional to the polarization of the fluorescence emission.

The fluoroscein-labelled probe—RBT0045864-FAM—

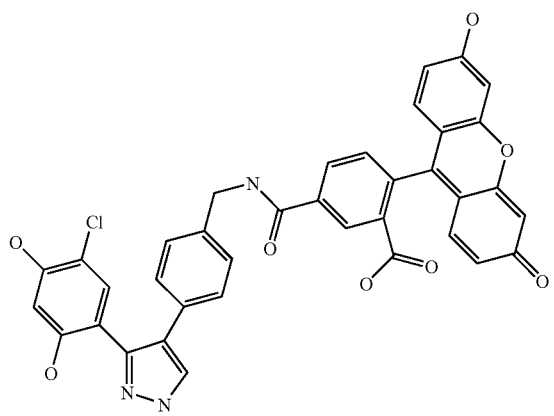

binds to HSP90 {full-length human, full-length yeast or N-terminal domain HSP90} and the anisotropy {rotation of the probe:protein complex} is measured.

Test compound is added to the assay plate, left to equilibrate and the anisotropy measured again. Any change in anisotropy is due to competitive binding of compound to HSP90, thereby releasing probe.

Materials

Chemicals are of the highest purity commercially available and all aqueous solutions are made up in AR water.

1) Costar 96-well black assay plate #3915
2) Assay buffer of (a)100 mM Tris pH7.4; (b) 20 mM KCl; (c) 6 mM $MgCl_2$. Stored at room temperature.
3) BSA (bovine serum albumen) 10 mg/ml (New England Biolabs # B9001S)
4) 20 mM probe in 100% DMSO stock concentration. Stored in the dark at RT. Working concentration is 200 nM diluted in AR water and stored at 4° C. Final concentration in assay 80 nM.
5) E. coli expressed human full-length HSP90 protein, purified >95% (see, e.g., Panaretou et al., 1998) and stored in 50 μL aliquots at −80° C.

Protocol

1) Add 100 μl 1× buffer to wells 11A and 12A (=FP BLNK)
2) Prepare assay mix—all reagents are kept on ice with a lid on the bucket as the probe is light-sensitive.

|  | i. Final Conc" |  |
|---|---|---|
| 1× Hsp90 FP Buffer | 10 ml | 1× |
| BSA 10 mg/ml (NEB) 5 μg/ml | 5.0 μl |  |
| Probe 200 μM 80 nM | 4.0 μl |  |

-continued

|  | i. Final Conc" |
|---|---|
| Human full-length Hsp90 200 nM | 6.25 μl |

3) Aliquot 100 μl assay mix to all other wells
4) Seal plate and leave in dark at room temp for 20 minutes to equilibrate Compound Dilution Plate—1×3 Dilution Series 1) In a clear 96-well v-bottom plate—{# VWR 007/008/257} add 10 μl 100% DMSO to wells B1 to H11
2) To wells A1 to A11 add 17.5 μl 100% DMSO
3) Add 2.5 μl cpd to A1. This gives 2.5 mM {50×} stock cpd—assuming cpds 20 mM.
4) Repeat for wells A2 to A10. Control in columns 11 and 12.
5) Transfer 5 μl from row A to row B—not column 12. Mix well.
6) Transfer 5 μl from row B to row C. Mix well.
7) Repeat to row G.
8) Do not add any compound to row H—this is the 0 row.
9) This produces a 1×3 dilution series from 50 μM to 0.07 μM.
10) In well B12 prepare 20 μl of 100 μM standard compound.
11) After first incubation the assay plate is read on a Fusion™ α-FP plate reader (Packard BioScience, Pangbourne, Berkshire,UK).
12) After the first read, 2 μl of diluted compound is added to each well for columns 1 to 10. In column 11 {provides standard curve} only add compound B11-H11. Add 2 μl of 100 mM standard cpd to wells B12-H12 {is positive control}
13) The Z' factor is calculated from zero controls and positive wells. It typically gives a value of 0.7-0.9.

The compounds tested in the above assay were assigned to one of two activity ranges, namely A=<10 μM; B=>10 μM, and those assignments are reported above.

A growth inhibition assay was also employed for the evaluation of candidate HSP90 inhibitors:

Assessment of Cytotoxicity by Sulforhodamine B (SRB) Assay: Calculation of 50% Inhibitory Concentration ($IC_{50}$).

Day 1

1) Determine cell number by haemocytometer.
2) Using an 8 channel multipipettor, add 160 μl of the cell suspension (3600 cells/well or 2×10⁴ cells/ml) to each well of a 96-well microtitre plate.
3) Incubate overnight at 37° C. in a $CO_2$ incubator.

Day 2

4) Stock solutions of drugs are prepared, and serial dilutions of each drug are performed in medium to give final concentrations in wells.
5) Using a multipipettor, 40 μl of drug (at 5× final concentration) is added to quadruplicate wells.
6) Control wells are at either side of the 96 well plates, where 40 μl of medium is added.
7) Incubate plates in $CO_2$ incubator for 4 days (48 hours).

Day 6

8) Tip off medium into sink and immerse plate slowly into 10% ice cold trichloroacetic acid (TCA). Leave for about 30 mins on ice.
9) Wash plates three times in tap water by immersing the plates into baths of tap water and tipping it off.
10) Dry in incubator.

11) Add 100 µl of 0.4% SRB in 1% acetic acid to each well (except the last row (right hand)of the 96 well plate, this is the 0% control, ie no drug, no stain. The first row will be the 100% control with no drug, but with stain). Leave for 15 mins.

12) Wash off unbound SRB stain with four washes of 1% acetic acid.

13) Dry plates in incubator.

14) Solubilise SRB using 100 µl of 10 mM Tris base and put plates on plate shaker for 5 mins.

15) Determine absorbance at 540 nm using a plate reader. Calculate mean absorbance for quadruplicate wells and express as a percentage of value for control, untreated wells.

16) Plot % absorbance values versus log drug concentration and determine the $IC_{50}$.

By way of illustration, the compound of Example 2 gave an IC50 in the 'A' range (<50 µM) for the SRB growth arrest assay.

REFERENCES

A number of publications are cited above in order to more fully describe and disclose the invention and the state of the art to which the invention pertains. Full citations for these references are provided below. Each of these references is incorporated herein by reference in its entirety into the present disclosure.

Argon Y and Simen B B. 1999 "Grp94, an ER chaperone with protein and peptide binding properties", *Semin. Cell Dev. Biol.*, Vol. 10, pp. 495-505.

Bijimakers M-J J E, Marsh M. 2000 "Hsp90 is essential for the synthesis and subsequent membrane association, but not the maintenance, of the Src-kinase p56lck", *Molecular Biology of the Cell, Vol.* 11(5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", *Brit. J. Pharmacol.*, Vol 131(1), pp. 13-16.

Chen C-F, Chen Y, Dai K D, Chen P-L, Riley D J and Lee W-H. 1996 "A new member of the hsp90 family of molecular chaperones interacts with the retinoblastoma protein during mitosis and after heat shock", *Mol. Cell. Biol.*, Vol.16, pp. 4691-4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", *Chem. Biol.*, Vol. 8, pp. 289-299.

Conroy S E and Latchman D S. 1996 "Do heat shock proteins have a role in breast cancer?", *Brit. J. Cancer*, Vol. 74, pp. 717-721.

Felts S J, Owen B A L, Nguyen P, Trepel J, Donner D B and Toft D O. 2000 "The HSP90-related protein TRAP1 is a mitochondrial protein with distinct functional properties", *J. Biol. Chem.*, Vol. 5, pp. 3305-3312.

Fuller W, Cuthbert A W. 2000 "Post-translational disruption of the delta F508 cystic fibrosis transmembrane conductance regulator (CFTR)-molecular Chaperone complex with geldanamycin stabilizes delta F508 CFTR in the rabbit reticulocyte lysate", *J. Biol. Chem.*; Vol 275(48), pp. 37462-37468.

Hickey E, Brandon S E, Smale G, Lloyd D and Weber L A. 1999 "Sequence and regulation of a gene encoding a human 89-kilodalton heat shock protein", *Mol. Cell. Biol.*, Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor I (HSF1) and prostate adenocarcinoma, *Am. J. Pathol.* Vol.156, pp. 857-864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", *Cancer Res.*, Vol. 61, pp. 4003-4009.

Hur E, Kim H-H, Choi S M, Kim J H, Yim S, Kwon H J, Choi Y, Kim D K, Lee M-O, Park H. 2002 "Reduction of hypoxia-induced transcription through the repression of hypoxia-inducible factor-1α/aryl hydrocarbon receptor nuclear translocator DNA binding by the 90-kDa heat-shock protein inhibitor radicicol", *Mol. Pharmacol.*, Vol 62(5), pp. 975-982.

Hutter etal, 1996, *Circulation*, Vol.94, pp.1408.

Jameel A, Skilton R A, Campbell T A, Chander S K, Coombes R C and Luqmani Y A. 1992 "Clinical and biological significance of HSP89a in human breast cancer", *Int. J. Cancer*, Vol. 50, pp. 409-415.

Jolly C and Morimoto R I. 2000 "Role of the heat shock response and molecular chaperones in oncogenesis and cell death", *J. Natl. Cancer Inst.*, Vol. 92, pp. 1564-1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", *Cancer*, Vol. 85, pp.1649-1657.

Kelland L R, Abel G, McKeage M J, Jones M, Goddard P M, Valenti M, Murrer B A and Harrap K R. 1993 "Preclinical antitumour evaluation of bis-acetalo-amino-dichloro-cyclohexylamine platinum (IV): an orally active platinum drug", *Cancer Research*, Vol. 53, pp. 2581-2586.

Kelland L R, Sharp S Y, Rogers P M, Myers T G and Workman P. 1999 "DT-diaphorase expression and tumor cell sensitivity to 17-allylamino, 17-demethoxygeldanamycin, an inhibitor of heat shock protein 90", *J. Natl. Cancer Inst.*, Vol. 91, pp.1940-1949.

Kurebayashi J, Otsuki T, Kurosumi M, Soga S, Akinaga S, Sonoo, H. 2001 "A radicicol derivative, KF58333, inhibits expression of hypoxia-inducible factor-1α and vascular endothelial growth factor, angiogenesis and growth of human breast cancer xenografts", *Jap. J. Cancer Res.*, Vol 92(12), 1342-1351.

Kwon H J, Yoshida M, Abe K, Horinouchi S and Bepple T. 1992 "Radicicol, an agent inducing the reversal of transformed phentoype of src-transformed fibroblasts, *Biosci., Biotechnol., Biochem.*, Vol. 56, pp. 538-539.

Lebeau J, Le Cholony C, Prosperi M T and Goubin G. 1991 "Constitutive overexpression of 89 kDa heat shock protein gene in the HBL100 mammary cell line converted to a tumorigenic phenotype by the EJ/T24 Harvey-ras oncogene", *Oncogene*, Vol. 6, pp.1125-1132.

Marcu M G, Chadli A, Bouhouche I, Catelli M and Neckers L. 2000a "The heat shock protein 90 antagonist novobiocin interacts with a previously unrecognized ATP-binding domain in the carboxyl terminus of the chaperone", *J. Biol. Chem.*, Vol. 275, pp. 37181-37186.

Marcu M G, Schulte T W and Neckers L. 2000b "Novobiocin and related coumarins and depletion of heat shock protein 90-dependent signaling proteins", *J. Natl. Cancer Inst.*, Vol. 92, pp. 242-248.

Martin K J, Kritzan B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", *Cancer Res.*, Vol. 60, pp. 2232-2238.

Neckers L, Schulte T W and Momnaaugh E. 1999 "Geldanamycin as a potential anti-cancer agent: its molecular target and biochemical activity", *Invest. New Drugs*, Vol.17, pp. 361-373.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", *Proc. Am. Assoc. Cancer Res.*, Vol. 38, pp. 308.

Panaretou B, Prodromou C, Roe S M, O'Brien R, Ladbury J E, Piper P W and Pearl L H. 1998 "ATP binding and hydrolysis are essential to the function of the HSP90 molecular chaperone in vivo", *EMBO J.*, Vol. 17, pp. 4829-4836.

Plumier etal, 1997, *Cell. Stress Chap.*, Vol.2, pp.162

Pratt W B. 1997 "The role of the HSP90-based chaperone system in signal transduction by nuclear receptors and receptors signalling via MAP kinase", *Annu. Rev. Pharmacol. Toxicol.*, Vol. 37, pp. 297-326.

Prodromou C and Pearl L H. 2000a "Structure and in vivo function of HSP90", *Curr. Opin. Struct. Biol.*, Vol.10, pp. 46-51.

Prodromou C, Roe S M, O'Brien R, Ladbury J E, Piper P W and Pearl L H. 1997 "Identification and structural characterization of the ATP/ADP-binding site in the HSP90 molecular chaperone", *Cell*, Vol. 90, pp. 65-75.

Prodromou C, Panaretou B, Chohan S, Siligardi G, O'Brien R, Ladbury J E, Roe S M, Piper P W and Pearl L H. 2000b "The ATPase cycle of HSP90 drives a molecular 'clamp' via transient dimerization of the N-terminal domains", *EMBO J.* Vol. 19, pp. 4383-4392.

Rajder etal, 2000, *Ann. Neurol.*, Vol.47, pp.782.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", *J. Med. Chem.*, Vol. 42, pp.260-266.

Rutherford S L and Lindquist S. 1998 "HSP90 as a capacitor for morphological evolution. *Nature*, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", *Mol. Endocrinology*, Vol. 13, pp.1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", *Cell Stress and Chaperones*, Vol. 3, pp.100-108.

Schulte T W and Neckers L M. 1998 "The benzoquinone ansamycin 17-allylamino-17-deemthoxygeldanamcyin binds to HSP90 and shares important biologic activities with geldanamcyin", *Cancer Chemother. Pharmacol.*, Vol.42, pp. 273-279.

Sittler etal, 2001, *Hum. Mol. Genet.*, Vol.10, pp.1307.

Smith D F. 2001 "Chaperones in signal transduction", in: *Molecular chaperones in the cell* (P Lund, ed.; Oxford University Press, Oxford and NY), pp.165-178.

Smith D F, Whitesell L and Katsanis E. 1998 "Molecular chaperones: Biology and prospects for pharmacological intervention", *Pharmacological Reviews*, Vol. 50, pp. 493-513.

Song H Y, Dunbar J D, Zhang Y X, Guo D and Donner D B. 1995 "Identification of a protein with homology to hsp90 that binds the type 1 tumour necrosis factor receptor", *J. Biol. Chem.*, Vol. 270, pp. 3574-3581.

Stebbins C E, Russo A, Schneider C, Rosen N, Hartl F U and Pavietich N P. 1997 "Crystal structure of an HSP90-geldanamcyin complex: targeting of a protein chaperone by an antitumor agent", *Cell*, Vol. 89, pp. 239-250.

Supko J G, Hickman R L, Grever M R and Malspeis L. 1995 "Preclinical pharmacologic evaluation of geldanamycin as an antitumour agent", *Cancer Chemother. Pharmacol.*, Vol. 36, pp. 305-315.

Tratzelt etal, 1995, *Proc. Nat. Acad. Sci.*, Vol. 92, pp. 2944.

Trost etal, 1998, *J. Clin. Invest.*, Vol.101, pp.855.

Tytell M and Hooper P L. 2001 "Heat shock proteins: new keys to the development of cytoprotective therapies", *Emerging Therapeutic Targets*, Vol. 5, pp. 267-287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", *Mol. Cell. Biol.*, Vol. 6, pp. 2198-2206.

Waxman, Lloyd H. Inhibiting hepatitis C virus processing and replication. (Merck & Co., Inc., USA). PCT Int. Appl. (2002), WO 0207761

Winklhofer etal, 2001, *J. Biol. Chem.*, Vol. 276, 45160.

Whitesell L, Mimnaugh E G, De Costa B, Myers C E and Neckers L M. 1994 "Inhibition of heat shock protein HSP90-pp60v-src heteroprotein complex formation by benzoquinone ansamycins: essential role for stress proteins in oncogenic transformation", *Proc. Natl. Acad. Sci. U S A.*, Vol. 91, pp. 8324-8328.

Yorgin et al. 2000 "Effects of geldanamycin, a heat-shock protein 90-binding agent, on T cell function and T cell nonreceptor protein tyrosine kinases", *J. Immunol.*, Vol 164(6), pp. 2915-2923.

Young J C, Moarefi I and Hartl F U. 2001 "HSP90: a specialized but essential protein-folding tool", *J. Cell. Biol.*, Vol.154, pp. 267-273.

Zhao J F, Nakano H and Sharma S. 1995 "Suppression of RAS and MOS transformation by radicicol", *Oncogene*, Vol. 11, pp. 161-173.

The invention claimed is:

1. A compound of formula (IA) or (IB) or a salt, or N-oxide thereof:

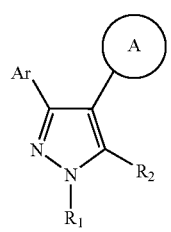

(IA)

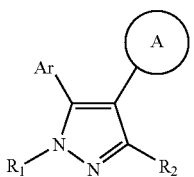

(IB)

wherein
Ar is a 2,4-dihydroxyphenyl group which is optionally further substituted in the 5-position,
$R_1$ and $R_2$ are independently hydrogen, methyl, ethyl, n- or iso-propyl, hydroxyethyl, or benzyl;
ring A is a ring of formula (IIA)

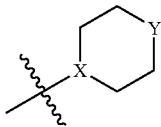

(IIA)

wherein X represents N, and Y represents CH, O, S or NH,
wherein (i) a ring carbon is optionally substituted, and/or (ii) a ring nitrogen is optionally substituted by a group of formula $-(Alk^1)_p-(Cyc)_n-(Alk^3)_m-(Z)_r-(Alk^2)_s-Q$ where $Alk^1$, $Alk^2$ and $Alk^3$ are optionally substituted $C_1$-$C_3$ alkyl,
Cyc is an optionally substituted phenylene radical;
m, n, p, r and s are independently 0 or 1,
Z is $-O-$, $-S-$, $-(C=O)-$, $-SO_2-$, $-C(=O)O-$, $-OC(=O)-$, $-NR^A-$, $-C(=O)NR^A-$, $-NR^AC(=O)-$, $-SO_2NR^A-$, or $-NR^ASO_2-$ wherein $R^A$ is hydrogen or $C_1$-$C_6$ alkyl, and
Q is an optionally substituted phenyl, pyridyl, furyl, thienyl, oxadiazolyl, imidazolyl, or morpholinyl wherein "optionally substituted" means substituted with up to four substituents, each of which is independently selected from $(C_1$-$C_6)$alkyl, $(C_1$-$C_6)$alkoxy, hydroxy, hydroxy$(C_1$-$C_6)$alkyl, mercapto, mercapto$(C_1$-$C_6)$alkyl, $(C_1$-$C6)$alkylthio, halo, trifluoromethyl, trifluoromethoxy, nitro, nitrile, oxo, phenyl, $-COOH$, $-COOR^A$, $-COR^A$, $-SO_2R^A$, $-CONH_2$, $-CONHNH_2$; $-CONHNHR^A$, $-CONHNR^AR^B$, $-SO_2NH_2$, $-CONHR^A$, $SO_2NHR^A$, $-CONR^AR^B$, $-SO_2NR^AR^B$, $-NH_2$, $-NHR^A$, $-NR^AR^B$, $-OCONH_2$, $-OCONHR^A$, $-OCONR^AR^B$, $-NHCOR^A$, $-NHCOOR^A$, $-NR^BCOOR^A$, $-NHSO_2OR^A$, $-NR^BSO_2OR^A$, $-NHCONH_2$, $-NR^ACONH_2$, $-NHCONHR^B$, $-NR^ACONHR^B$, $-NHCONR^AR^B$, and $-NR^ACONR^AR^B$ wherein $R^A$ and $R^B$ are independently a $(C_1$-$C_6)$alkyl group.

2. A compound as claimed in claim 1 wherein $R_1$ and $R_2$ are each hydrogen.

3. A compound as claimed in claim 2 wherein in the ring of formula (IIA), Y is $-NR^A-$ wherein $R^A$ is a radical of formula $-(Alk^1)_s-Q$, wherein $Alk^1$ is a $C_1$-$C_3$ alkylene radical and Q is optionally substituted phenyl, pyridyl, furyl, thienyl, oxadiazolyl, imidazolyl or morpholinyl, wherein optionally substituted means substituted with up to four substituents, each of which is independently selected from $(C_1$-$C_6)$alkyl, $(C_1$-$C_6)$alkoxy, hydroxy, hydroxy$(C_1$-$C_6)$alkyl, mercapto, mercapto$(C_1$-$C_6)$alkyl, $(C_1$-$C_6)$alkylthio, halo, trifluoromethyl, trifluoromethoxy, nitro, nitrile, oxo, phenyl, $-COOH$, $-COOR^A$, $-COR^A$, $-SO_2R^A$, $-CONH_2$, $-CONHNH_2$; $-CONHNHR^A$, $-CONHNR^AR^B$, $-SO_2NH_2$, $-CON$-$HR^A$, $SO_2NHR^A$, $-CONR^AR^B$, $-SO_2NR^AR^B$, $-NH_2$, $-NHR^A$, $-NR^AR^B$, $-OCONH_2$, $-OCONHR^A$, $-OCONR^AR^B$, $-NHCOR^A$, $-NHCOOR^A$, $-NR^BCOOR^A$, $-NHSO_2OR^A$, $-NR^BSO_2OR^A$, $-NHCONH_2$, $-NR^ACONH_2$, $-NHCONHR^B$, $-NR^ACONHR^B$, $-NHCONR^AR^B$, and $-NR^ACONR^AR^B$ wherein $R^A$ and $R^B$ are independently a $(C_1$-$C_6)$alkyl group.

4. A compound as claimed in claim 2 wherein in the ring of formula (IIA), Y is $-NR^A-$ wherein $R^A$ is a radical of formula $-(Alk^1)_p-(Cyc)_n-(Alk^3)_m-(Z)_r-(Alk^2)_s-Q$ wherein $Alk^1$, $Alk^2$, and $Alk^3$ are optionally substituted $C_1$-$C_3$ alkyl,
Cyc is an optionally substituted phenylene radical;
Z is $-O-$, $-S-$, $-(C=O)-$, $-SO_2-$, $-C(=O)O-$, $-OC(=O)-$, $-NR^A-$, $-C(=O)NR^A-$, $-NR^AC(=O)-$, $-SO_2NR^A-$, or $-NR^ASO_2-$ wherein $R^A$ is hydrogen or $C_1$-$C_6$ alkyl, and
Q is an optionally substituted phenyl, pyridyl, furyl, thienyl, oxadiazolyl, imidazolyl, or morpholinyl wherein "optionally substituted" means substituted with up to four substituents, each of which is independently selected from $(C_1$-$C_6)$alkyl, $(C_1$-$C_6)$ alkoxy, hydroxy, hydroxy$(C_1$-$C_6)$alkyl, mercapto, mercapto$(C_1$-$C_6)$ alkyl, $(C_1$-$C6)$alkylthio, halo, trifluoromethyl, trifluoromethoxy, nitro, nitrile, oxo, phenyl $-COOH$, $-COOR^A$, $-COR^A$, $-SO_2R^A$, $-CONH_2$, $-CONHNH_2$; $-CONHNHR^A$, $-CONHNR^AR^B$, $-SO_3NH_2$, $-CONHR^A$, $SO_2NHR^A$, $-CONR^AR^B$, $-SO_2NR^AR^B$, $-NH_2$, $-NHR^A$, $-NR^AR^B$, $-OCONH_2$, $-OCONHR^A$, $-OCONR^AR^B$, $-NH$-$COR^A$, $-NHCOOR^A$, $-NR^BCOOR^A$, $-NHSO_2OR^A$, $-NR^BSO_2OR^A$, $-NHCONH_2$, $-NR^ACONH_2$, $-NHCONHR^B$, $-NR^ACONHR^B$, $-NHCONR^AR^B$, and $-NR^ACONR^AR^B$ wherein $R^A$ and $R^B$ are independently a $(C_1$-$C_6)$alkyl group.

5. A compound of formula (IC) or (ID) or a salt, or N-oxide thereof:

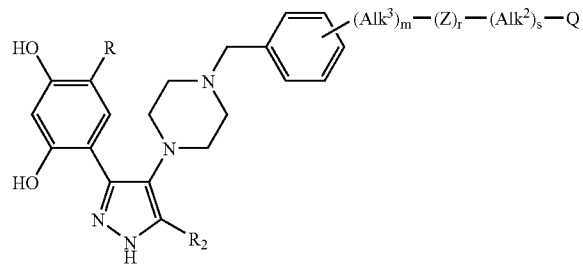

(IC)

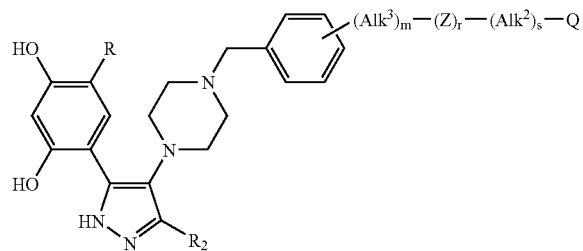

(ID)

wherein R is hydrogen, chloro, bromo, or a phenylethyl group which is optionally substituted in the phenyl ring, and $R_2$ is independently hydrogen, methyl, ethyl, n- or iso-propyl, hydroxyethyl, or benzyl;

$Alk^2$ and $Alk^3$ are optionally substituted $C_1$-$C_3$ alkyl, m, r and s are independently 0 or 1, Z is —O—, —S—, —(C=O)—, —SO$_2$—, —C(=O)O—, —OC(=O)—, —NR$^A$—, —C(=O)NR$^A$—, —NR$^A$C(=O)—, —SO$_2$NR$^A$—, or —NR$^A$SO$_2$— wherein $R^A$ is hydrogen or $C_1$-$C_6$ alkyl, and Q is an optionally substituted phenyl, pyridyl, furyl, thienyl, oxadiazolyl, imidazolyl, or morpholinyl, wherein "optionally substituted" means substituted with up to four substituents, each of which is independently selected from ($C_1$-$C_6$)alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, halo, trifluoromethyl, trifluoromethoxy, nitro, nitrile, oxo, phenyl, —COOH, —COOR$^A$, —COR$^A$, —SO$_2$R$^A$, —CONH$_2$, —CONHNH$_2$; —CONHNHR$^A$, —CONHNR$^A$R$^B$, —SO$_2$NH$_2$, —CONHR$^A$, SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, and —NR$^A$CONR$^A$R$^B$ wherein $R^A$ and $R^B$ are independently a ($C_1$-$C_6$)alkyl group.

6. A compound as claimed in claim 5 wherein m is 0, r is 1, and Z is —C(=O)NH—.

7. A compound of formula (IA) or (IB) or a salt, or N-oxide thereof:

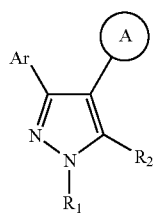

(IA)

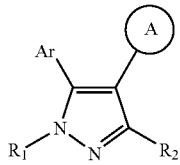

(IB)

wherein

Ar is a 2,4-dihydroxyphenyl group which is further substituted in the 5-position by chloro or bromo; or by optionally substituted phenyl or $C_1$-$C_6$ alkyl; or by a phenylethyl group which is optionally substituted in the phenyl ring thereof, $R_1$ and $R_2$ are independently hydrogen, methyl, ethyl, n- or iso-propyl, hydroxyethyl, or benzyl;

ring A is a ring of formula (IIA)

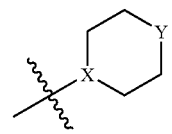

(IIA)

wherein X represents N, and Y represents NR$^A$ wherein $R^A$ is a radical of formula -(Alk$^1$)$_s$-Q, wherein Alk$^1$ is a $C_1$-$C_3$ alkylene radical and Q is optionally substituted phenyl, pyridyl, furyl, thienyl, oxadiazolyl, imidazolyl or morpholinyl, wherein optionally substituted means substituted with up to four substituents, each of which is independently selected from ($C_1$-$C_6$)alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, halo, trifluoromethyl, trifluoromethoxy, nitro, nitrile, oxo, phenyl, —COOH, —COOR$^A$, —COR$^A$, —SO$_2$R$^A$, —CONH$_2$, —CONHNH$_2$; —CONHNHR$^A$, —CONHNR$^A$R$^B$, —SO$_2$NH$_2$, —CONHR$^A$, SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, and —NR$^A$CONR$^A$R$^B$ wherein $R^A$ and $R^B$ are independently a ($C_1$-$C_6$)alkyl group.

* * * * *

UNITED STATES PATENT AND TRADEMARK OFFICE
CERTIFICATE OF CORRECTION

PATENT NO.         : 7,612,201 B2                                   Page 1 of 1
APPLICATION NO.    : 10/536899
DATED              : November 3, 2009
INVENTOR(S)        : Mandy Christine Beswick et al.

It is certified that error appears in the above-identified patent and that said Letters Patent is hereby corrected as shown below:

Title page, Item [*] Delete the phrase "by 315 days" and insert -- by 706 days --.

In Column 76, Claim 4, Line 28:
    Please remove "($C_1$-C6)" and insert -- ($C_1$-$C_6$) --.

In Column 76, Claim 4, Line 32:
    Please remove "-$SO_s$$NH_2$"and insert -- -$SO_2$$NH_2$ --.

In Column 78, Claim 7, Line 13:
    Please remove "by chioro or" and insert -- by chloro or --.

Signed and Sealed this

Thirty-first Day of August, 2010

David J. Kappos
*Director of the United States Patent and Trademark Office*